United States Patent
Yofu et al.

(10) Patent No.: US 9,070,887 B2
(45) Date of Patent: *Jun. 30, 2015

(54) PHOTOELECTRIC CONVERSION DEVICE, PHOTOELECTRIC CONVERSION DEVICE MATERIAL, PHOTOSENSOR AND IMAGING DEVICE

(71) Applicant: FUJIFILM Corporation, Tokyo (JP)

(72) Inventors: Katsuyuki Yofu, Kanagawa (JP); Kimiatsu Nomura, Kanagawa (JP); Mitsumasa Hamano, Kanagawa (JP); Tetsuro Mitsui, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 95 days.

This patent is subject to a terminal disclaimer.

(21) Appl. No.: 13/945,122

(22) Filed: Jul. 18, 2013

(65) Prior Publication Data

US 2013/0299799 A1    Nov. 14, 2013

Related U.S. Application Data

(62) Division of application No. 12/891,897, filed on Sep. 28, 2010, now Pat. No. 8,525,577.

(30) Foreign Application Priority Data

Sep. 29, 2009   (JP) ................................. 2009-225522

(51) Int. Cl.
    *H01L 29/08*    (2006.01)
    *H01L 35/24*    (2006.01)
    (Continued)

(52) U.S. Cl.
    CPC ................. *H01L 51/42* (2013.01); *B82Y 10/00* (2013.01); *H01L 27/307* (2013.01);
    (Continued)

(58) Field of Classification Search
    USPC ............. 257/40, E51.041; 327/514; 544/300; 548/440, 527; 549/43, 50, 57, 59, 68, 549/74
    See application file for complete search history.

(56) References Cited

U.S. PATENT DOCUMENTS 5,965,875 A    10/1999 Merrill
2004/0065867 A1    4/2004 Hartmann et al.
(Continued)

FOREIGN PATENT DOCUMENTS

JP    05-129576 A    5/1993
JP    2002-76391 A    3/2002
(Continued)

OTHER PUBLICATIONS

Office Action dated Dec. 13, 2013, issued by the State Intellectual Property Office of the People's Republic of China in counterpart Chinese Application No. 201010297157.7.
(Continued)

*Primary Examiner* — Bijan Ahvazi
(74) *Attorney, Agent, or Firm* — Sughrue Mion, PLLC

(57) ABSTRACT

A photoelectric conversion device comprising an electrically conductive film, an organic photoelectric conversion film, and a transparent electrically conductive film, wherein the organic photoelectric conversion film contains a compound represented by the following formula (1) and an n-type organic semiconductor:

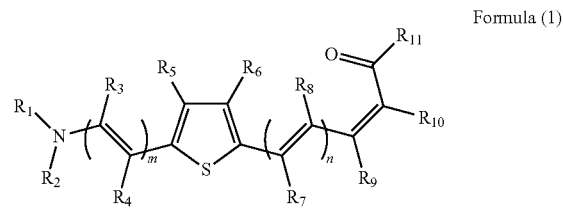

Formula (1)

wherein each of $R_1$ and $R_2$ independently represents a substituted aryl group, an unsubstituted aryl group, a substituted heteroaryl group or an unsubstituted heteroaryl group, each of $R_3$ to $R_{11}$ independently represents a hydrogen atom or a substituent provided that an acidic group is excluded, m represents 0 or 1, n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, or $R_{10}$ and $R_{11}$ may be combined each other to form a ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

5 Claims, 6 Drawing Sheets

(51) Int. Cl.
*H01L 51/00* (2006.01)
*H01L 51/42* (2006.01)
*B82Y 10/00* (2011.01)
*C07D 411/00* (2006.01)
*H01L 27/30* (2006.01)

(52) U.S. Cl.
CPC ........ *H01L 51/0046* (2013.01); *H01L 51/0053* (2013.01); *H01L 51/006* (2013.01); *H01L 51/0061* (2013.01); *H01L 51/0068* (2013.01); *H01L 51/0072* (2013.01); *H01L 51/0074* (2013.01); *H01L 51/4253* (2013.01); *Y02E 10/549* (2013.01)

(56) References Cited

U.S. PATENT DOCUMENTS

| 2007/0068450 | A1* | 3/2007 | Jung et al. ................ 117/89 |
| 2009/0085029 | A1 | 4/2009 | Mitsui et al. |
| 2009/0189058 | A1* | 7/2009 | Mitsui et al. ............. 250/208.1 |
| 2010/0140559 | A1 | 6/2010 | Klaus et al. |

FOREIGN PATENT DOCUMENTS

| JP | 2003-332551 A | 11/2003 |
| JP | 2004-526707 A | 9/2004 |
| JP | 2005-132914 A | 5/2005 |
| JP | 2007-91714 A | 4/2007 |
| JP | 2007-123707 A | 5/2007 |
| JP | 2009-088291 A | 4/2009 |
| JP | 2009-200482 A | 9/2009 |
| WO | 2007-017475 A1 | 2/2007 |
| WO | 2009-007340 A1 | 1/2009 |

OTHER PUBLICATIONS

Office Action dated Oct. 15, 2013, issued by the Japanese Patent Office in counterpart Japanese Application No. 2009-225522.
Office Action dated Aug. 18, 2014, issued by the State Intellectual Property Office of the People's Republic of China in counterpart Chinese Application No. 201010297157.7.
Office Action dated Aug. 19, 2014, issued by the Taiwanese Intellectual Property Office in counterpart Taiwanese Application No. 099133070.
C. W. Tang, "Two-layer organic photovoltaic cell", Appl. Phys. Lett., vol. 48, No. 2, pp. 183-185 (Jan. 13, 1986).
Sophie Roquet et al., "Triphenylamine—Thienylenevinylene Hybird Systems with Internal Charge Transfer as Donor Materials for Heterjunction Solar Cells", 128 J. Am. Chem. Soc. pp. 3459-3466 (2006).
Nils M. Kronenberg et al., "Bulk heterojunction organic solar cells based on merocyanine colorants", Chem Commun. pp. 6489-6491 (The Royal Society of Chemistry 2008).
Extended European Search Report issued Mar. 24, 2011 in European Application No. 10 181 955.5.
Office Action dated Feb. 6, 2013 in European Application No. 10 181 955.5.
Office Action dated Feb. 16, 2015, issued by the State Intellectual Property Office of the People's Republic of China in counterpart Chinese Application No. 201010297157.7.

* cited by examiner

PHOTOELECTRIC CONVERSION DEVICE, PHOTOELECTRIC CONVERSION DEVICE MATERIAL, PHOTOSENSOR AND IMAGING DEVICE

CROSS-REFERENCE TO RELATED APPLICATION

This is a Divisional Application of U.S. application Ser. No. 12/891,897 filed Sep. 28, 2010, which claims priority from Japanese Patent Application No. 2009-225522 filed Sep. 29, 2009. The entire disclosures of the prior applications are hereby incorporated by reference in their entirety.

BACKGROUND OF THE INVENTION

1. Field of the Invention

The present invention relates to a photoelectric conversion device, a photoelectric conversion device material, a photosensor and an imaging device.

2. Description of the Related Art

Conventional photosensors in general are a device fabricated by forming a photodiode (PD) in a semiconductor substrate such as silicon (Si). As for the solid-state imaging device, there is widely used a flat solid-state imaging device where PD are two-dimensionally arrayed in a semiconductor substrate and a signal according to a signal charge generated by photoelectric conversion in each PD is read out through a CCD or CMOS circuit.

The method for realizing a color solid-state imaging device is generally fabrication of a structure where on the light incident surface side of the flat solid-state imaging device, a color filter transmitting only light at a specific wavelength is disposed for color separation. In particular, a single-plate solid-state imaging device in which color filters transmitting blue (B) light, green (G) light and red (R) light, respectively, are regularly disposed on each of two-dimensionally arrayed PD is well known as a system widely used at present in a digital camera and the like.

In this single-plate solid-state imaging device, since the color filter transmits only light at a limited wavelength, light failed in transmitting through the color filter is not utilized and the light utilization efficiency is bad. Also, in recent years, fabrication of a multipixel device is proceeding, and the pixel size and in turn, the area of a photodiode part become small, which brings about problems of reduction in the aperture ratio and reduction in the light collection efficiency.

In order to solve these problems, a system of stacking, in the longitudinal direction, photoelectric conversion parts capable of detecting light at different wavelengths has been proposed. As regards such a system, in so far as visible light is concerned, there are disclosed, for example, a system utilizing wavelength dependency of the absorption coefficient of Si, where a vertical stack structure is formed and colors are separated by the difference in the depth (Patent Document 1), and a system where a first light-receiving part using an organic semiconductor and second and third light-receiving parts each composed of Si are formed (Patent Document 2).

However, such a system is disadvantageous in that the color separation is poor, because the absorption range is overlapped among respective light-receiving parts in the depth direction of Si and the spectroscopic property is bad.

Also, development of a solid-state imaging device having a structure where an organic photoelectric conversion film is formed on a signal read-out substrate is proceeding.

In such a solid-state imaging device, it is a task particularly to enhance the photoelectric conversion efficiency or reduce the dark current, and as a method for improving these properties, there are disclosed, for example, introduction of a pn-junction (Non-Patent Document 1) or introduction of a bulk heterojunction structure (Patent Document 3) for the former and introduction of a blocking layer (Patent Document 4) for the latter.

In the case of increasing the photoelectric conversion efficiency by the introduction of pn-junction or bulk heterojunction structure, an increase in the dark current often becomes a problem. Also, the degree of improvement in the photoelectric conversion efficiency differs depending on the combination of materials and in some cases, the ratio of photosignal amount/dark time noise does not increase from that before introduction of such a structure. In employing the method above, what materials are combined is important and in particular, when reduction in the dark time noise is intended, this is difficult to achieve by conventionally reported combinations of materials.

As the literature describing a photoelectric conversion device using an organic material, Patent Documents 5 to 7, Non-Patent Documents 2 and 3, and the like are also known.

Patent Document 5 describes a device using an organic photoelectric conversion film containing fullerenes, but it is impossible only by fullerenes to satisfy all of the above-described high photoelectric conversion efficiency, low dark current and high light absorption.

Patent Document 6 describes a heterocyclic compound containing thiophene, furan or pyrrole, and Patent Document 7 and Non-Patent Documents 2 and 3 describe a solar cell by an organic photoelectric conversion device using a thiophene derivative and a fullerene derivative.

| | |
|---|---|
| [Patent Document 1] | U.S. Pat. No. 5,965,875 |
| [Patent Document 2] | JP-A-2003-332551 (the term "JP-A" as used herein means an "unexamined published Japanese patent application") |
| [Patent Document 3] | JP-A-2002-076391 |
| [Patent Document 4] | JP-A-5-129576 |
| [Patent Document 5] | JP-A-2007-123707 |
| [Patent Document 6] | JP-A-2005-132914 |
| [Patent Document 7] | JP-A-2007-091714 |
| [Non-Patent Document 1] | Appl. Phys. Lett., 1986, 48, 183 |
| [Non-Patent Document 2] | J. Am. Chem. Soc., 2006, 128, 3459 |
| [Non-Patent Document 3] | Chem. Commun., 2008, 48, 6489 |

SUMMARY OF THE INVENTION

However, the devices of Patent Documents 5 to 7 and Non-Patent Documents 2 and 3 are a device aiming at use as a solar cell, and neither disclosure about dark current reduction and the like is found nor application and the like to a photoelectric conversion device for use in an imaging device is referred to.

An object of the present invention is to provide a photoelectric conversion device using an organic photoelectric conversion film, particularly a photoelectric conversion device excellent in the photoelectric conversion efficiency, and a solid-state imaging device.

In an organic photoelectric conversion device, for realizing high light absorptivity, high photoelectric conversion efficiency and low dark current, the organic photoelectric conversion film used preferably satisfies the following requirements.

1. The molar extinction coefficient of the dye needs to be high.
2. In terms of high efficiency, the signal charge after dissociation of an exciton needs to be swiftly transmitted to both electrodes without loss. High mobility and high charge transportability with a small number of carrier trapping sites are necessary.

3. In terms of high photoelectric conversion efficiency, it is preferred that the exciton stabilizing energy is small and the exciton can be swiftly dissociated by the effect of an externally applied electric field or an electric field generated in the inside by pn-junction or the like (high exciton dissociation efficiency).

4. In order to reduce as much the carrier generated in the inside at dark time as possible, it is preferred to select a film structure or material that allows little presence of an intermediate level in the inside or impurities working out to one of causes thereof.

5. In the case of stacking a plurality of layers, an energy level matching the adjacent layer is required and if an energetic barrier is formed, this inhibits charge transport.

In the case of forming the organic photoelectric conversion film by a vapor deposition method, the decomposition temperature is preferably higher than the temperature allowing for vapor deposition, because the thermal decomposition during vapor deposition can be suppressed. The coating method is advantageous in that the film can be formed without subjecting to limitation by the decomposition above and a low cost can be realized, but film formation by a vapor deposition method is preferred because uniform film formation is facilitated and possible mixing of impurities can be reduced.

As a result of intensive studies, the present inventors have found a high-absorption material capable of realizing high photoelectric conversion efficiency and low dark current.

According to the studies by the present inventors, it has been found that when a compound represented by the following formula (1) and an n-type semiconductor are used in combination, a photoelectric conversion device excellent in the photoelectric conversion efficiency is obtained. Also, it has been found that out of the compounds represented by the following formula (1), a compound represented by the following formula (4) and a compound represented by formula (5) are a novel compound useful as a photoelectric conversion material.

That is, the above-described object can be attained by the following techniques.

[1] A photoelectric conversion device comprising an electrically conductive film, an organic photoelectric conversion film, and a transparent electrically conductive film, wherein the organic photoelectric conversion film contains a compound represented by the following formula (1) and an n-type organic semiconductor:

Formula (1)

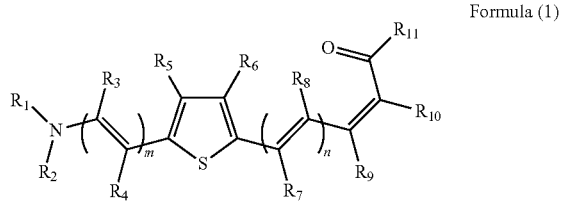

wherein each of $R_1$ and $R_2$ independently represents a substituted aryl group, an unsubstituted aryl group, a substituted heteroaryl group or an unsubstituted heteroaryl group, each of $R_3$ to $R_{11}$ independently represents a hydrogen atom or a substituent provided that an acidic group is excluded, m represents 0 or 1, n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, or $R_{10}$ and $R_{11}$ may be combined each other to form a ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

[2] The photoelectric conversion device according to the above [1], wherein the compound represented by formula (1) is a compound represented by the following formula (2):

Formula (2)

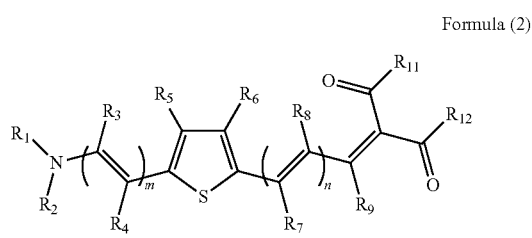

wherein $R_1$ to $R_9$, m and n have the same meanings as above, each of $R_{11}$ and $R_{12}$ independently represents a hydrogen atom or a substituent, and $R_{11}$ and $R_{12}$ may be combined each other to form a ring.

[3] The photoelectric conversion device according to the above [2], wherein the compound represented by formula (2) is a compound represented by the following formula (3):

Formula (3)

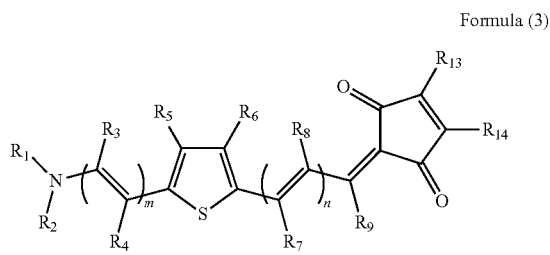

wherein $R_1$ to $R_9$, m and n have the same meanings as above, each of $R_{13}$ and $R_{14}$ independently represents a hydrogen atom or a substituent, and $R_{13}$ and $R_{14}$ may be combined each other to form a ring.

[4] The photoelectric conversion device according to the above [3], wherein the compound represented by formula (3) is a compound represented by the following formula (4):

Formula (4)

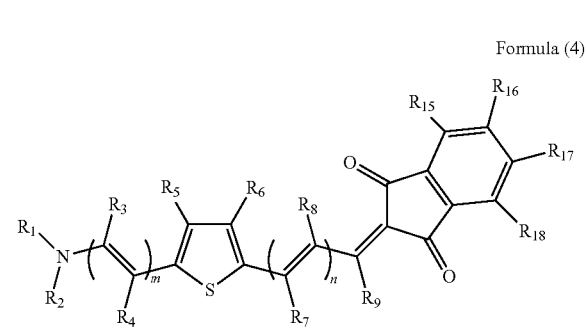

wherein $R_1$ to $R_9$, m and n have the same meanings as above, each of $R_{15}$ to $R_{18}$ independently represents a hydrogen atom or a substituent, and $R_{15}$ and $R_{16}$, $R_{16}$ and $R_{17}$, or $R_{17}$ and $R_{18}$ may be combined each other to form a ring.

[5] The photoelectric conversion device according to the above [3], wherein the compound represented by formula (3) is a compound represented by the following formula (5):

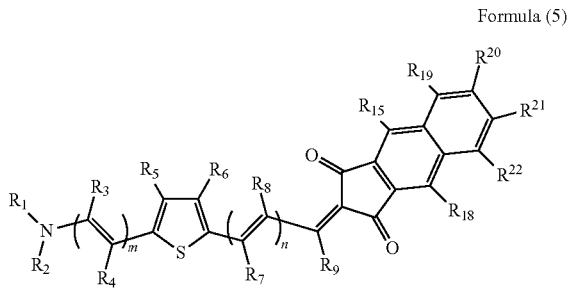

Formula (5)

wherein $R_1$ to $R_9$, m and n have the same meanings as above, each of $R_{15}$ and $R_{18}$ to $R_{22}$ independently represents a hydrogen atom or a substituent, and $R_{15}$ and $R_{19}$, $R_{19}$ and $R_{20}$, $R_{20}$ and $R_{21}$, $R_{21}$ and $R_{22}$, or $R_{22}$ and $R_{18}$ may be combined each other to form a ring.

[6] The photoelectric conversion device according to any one of the above [1] to [5], wherein the n-type organic semiconductor is a fullerene or a fullerene derivative.

[7] The photoelectric conversion device according to any one of the above [1] to [6], further comprising an electron blocking film.

[8] The photoelectric conversion device according to the above [7], wherein the electrically conductive film, the electron blocking film, the organic photoelectric conversion film and the transparent electrically conductive film are stacked in this order or the electrically conductive film, the organic photoelectric conversion film, the electron blocking film and the transparent electrically conductive film are stacked in this order.

[9] The photoelectric conversion device according to any one of the above [1] to [8], wherein n in formula (1) represents any integer of 0 to 3.

[10] The photoelectric conversion device according to any one of the above [6] to [9], wherein the volume ratio of the fullerene or fullerene derivative to the compound represented by formula (1) (fullerene or fullerene derivative/compound represented by formula (1)×100(%)) is 50% or more.

[11] The photoelectric conversion device according to any one of the above [1] to [10], wherein light is incident on the organic photoelectric conversion film through the transparent electrically conductive film.

[12] The photoelectric conversion device according to any one of the above [1] to [11], wherein the transparent electrically conductive film comprises a transparent electrically conductive oxide.

[13] The photoelectric conversion device according to any one of the above [1] to [12], wherein the transparent electrically conductive film is stacked directly on the organic photoelectric conversion film.

[14] A use method of the photoelectric conversion device according to any one of the above [1] to [13], with the electrically conductive film and the transparent electrically conductive film defining a pair of electrodes, the method comprising applying an electric field of $1 \times 10^{-4}$ to $1 \times 10^7$ V/cm between the pair of electrodes.

[15] A photosensor comprising the photoelectric conversion device according to any one of the above [1] to [13].

[16] An imaging device containing the photoelectric conversion device according to any one of the above [1] to [13].

[17] A compound represented by the following formula (4):

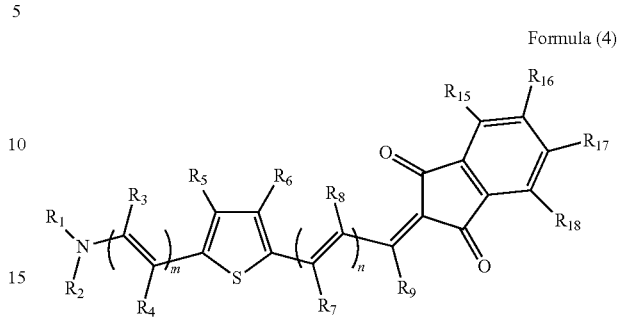

Formula (4)

wherein each of $R_1$ and $R_2$ independently represents a substituted aryl group, an unsubstituted aryl group, a substituted heteroaryl group or an unsubstituted heteroaryl group, each of $R_3$ to $R_9$ and $R_{15}$ to $R_{18}$ independently represents a hydrogen atom or a substituent, m represents 0 or 1, and n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, $R_{15}$ and $R_{16}$, $R_{16}$ and $R_{17}$, or $R_{17}$ and $R_{18}$ may be combined each other to form a ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

[18] A compound represented by the following formula (5):

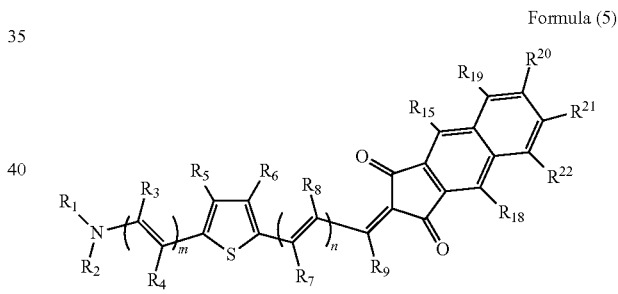

Formula (5)

wherein each of $R_1$ and $R_2$ independently represents a substituted aryl group, an unsubstituted aryl group, a substituted heteroaryl group or an unsubstituted heteroaryl group, each of $R_3$ to $R_9$, $R_{15}$ and $R_{18}$ to $R_{22}$ independently represents a hydrogen atom or a substituent, m represents 0 or 1, and n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, $R_{15}$ and $R_{19}$, $R_{19}$ and $R_{20}$, $R_{20}$ and $R_{21}$, $R_{21}$ and $R_{22}$, or $R_{22}$ and $R_{18}$ may be combined each other to form a ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

[19] A photoelectric conversion device comprising an electrically conductive film, an organic photoelectric conversion film, and a transparent electrically conductive film, wherein the organic photoelectric conversion film contains the compound according to the above [17] or [18].

[20] A photosensor comprising the photoelectric conversion device according to the above [19].

[21] An imaging device containing the photoelectric conversion device according to the above [19].

According to the present invention, an organic photoelectric conversion device and a solid-state imaging device, which are excellent in the photoelectric conversion efficiency, can be provided.

DESCRIPTION OF REFERENCE NUMERALS AND SIGNS

Figure 1A:
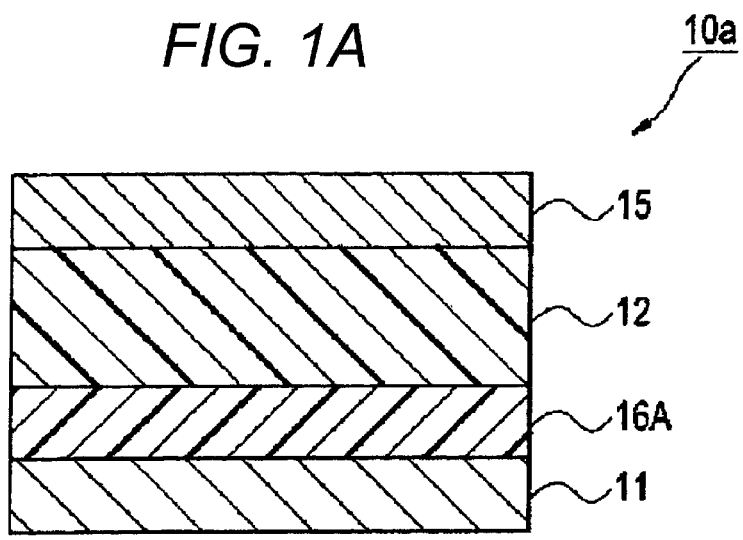
FIG. 1A and FIG. 1B each is a schematic cross-sectional view showing one configuration example of a photoelectric conversion device.

11 Lower electrode (electrically conductive film)
12 Photoelectric conversion layer (photoelectric conversion film)
15 Upper electrode (transparent electrically conductive film)
16A Electron blocking layer
16B Hole blocking layer
100, 200, 300, 400 Imaging Device

DETAILED DESCRIPTION OF THE INVENTION

The embodiments of the photoelectric conversion device according to the present invention are described below.

[Substituent W]

The substituent W is described below.

The substituent W includes a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may also be called a heteroring group), a cyano group, a hydroxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, an alkylsulfinyl group, an arylsulfinyl group, an alkylsulfonyl group, an arylsulfonyl group, an acyl group, an aryloxycarbonyl group, an alkoxycarbonyl group, an alkylcarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group and other known substituents.

More preferably, W represents, for example, the following (1) to (17):

(1) a halogen atom,
such as fluorine atom, chlorine atom, bromine atom and iodine atom;

(2) an alkyl group,
a linear, branched or cyclic alkyl group:
(2-a) an alkyl group,
preferably an alkyl group having a carbon number of 1 to 30 (e.g., methyl, ethyl, n-propyl, isopropyl, tert-butyl, n-octyl, eicosyl, 2-chloroethyl, 2-cyanoethyl, 2-ethylhexyl), and
(2-b) a cycloalkyl group,
preferably a substituted or unsubstituted cycloalkyl group having a carbon number of 3 to 30 (e.g., cyclohexyl, cyclopentyl, 4-n-dodecylcyclohexyl);

(3) an alkenyl group,
a linear, branched or cyclic alkenyl group having a carbon number of 2 to 30 (e.g., vinyl, allyl, styryl);

(4) an alkynyl group,
preferably an alkynyl group having a carbon number of 2 to 30 (e.g., ethynyl, propargyl, trimethylsilylethynyl);

(5) an aryl group,
preferably an aryl group having a carbon number of 6 to 30 (e.g., phenyl, p-tolyl, naphthyl, m-chlorophenyl, o-hexadecanoylaminophenyl, ferrocenyl);

(6) a heterocyclic group,
preferably a monovalent group obtained by removing one hydrogen atom from a 5- or 6-membered aromatic or non-aromatic heterocyclic compound, more preferably a 5- or 6-membered aromatic heterocyclic group having a carbon number of 2 to 50 (e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio);

(7) an alkoxy group,
preferably an alkoxy group having a carbon number of 1 to 30 (e.g., methoxy, ethoxy, isopropoxy, tert-butoxy, n-octyloxy, 2-methoxyethoxy);

(8) an aryloxy group,
preferably an aryloxy group having a carbon number of 6 to 30 (e.g., phenoxy, 2-methylphenoxy, 4-tert-butylphenoxy, 3-nitrophenoxy, 2-tetradecanoylaminophenoxy);

(9) an amino group,
preferably an amino group, an alkylamino group having a carbon number of 1 to 30, or an anilino group having a carbon number of 6 to 30 (e.g., amino, methylamino, dimethylamino, anilino, N-methyl-anilino and diphenylamino);

(10) an alkylthio group,
preferably an alkylthio group having a carbon number of 1 to 30 (e.g., methylthio, ethylthio, n-hexadecylthio);

(11) an arylthio group,
preferably an arylthio group having a carbon number of 6 to 30 (e.g., phenylthio, p-chlorophenylthio, m-methoxyphenylthio);

(12) a heterocyclic thio group,
preferably a substituted or unsubstituted heterocyclic thio group having a carbon number of 2 to 30 (e.g., 2-benzothiazolylthio, 1-phenyltetrazol-5-ylthio);

(13) an alkyl- or aryl-sulfinyl group,
preferably a substituted or unsubstituted alkylsulfinyl group having a carbon number of 1 to 30, or a substituted or unsubstituted arylsulfinyl group having a carbon number of 6 to 30 (e.g., methylsulfinyl, ethylsulfinyl, phenylsulfinyl and p-methylphenylsulfinyl);

(14) an alkyl- or aryl-sulfonyl group,
preferably an alkylsulfonyl group having a carbon number of 1 to 30, or an arylsulfonyl group having a carbon number of 6 to 30 (e.g., methylsulfonyl, ethylsulfonyl, phenylsulfonyl and p-methylphenylsulfonyl);

(15) an acyl group,
preferably a formyl group, an alkylcarbonyl group having a carbon number of 2 to 30, an arylcarbonyl group having a carbon number of 7 to 30, or a heterocyclic carbonyl group having a carbon number of 4 to 30 and being bonded to a carbonyl group through a carbon atom (e.g., acetyl, pivaloyl, 2-chloroacetyl, stearoyl, benzoyl, p-n-octyloxyphenylcarbonyl, 2-pyridylcarbonyl and 2-furylcarbonyl);

(16) a phosphino group,
preferably a phosphino group having a carbon number of 2 to 30 (e.g., dimethylphosphino, diphenylphosphino, methylphenoxyphosphino); and

(17) a silyl group,
preferably a silyl group having a carbon number of 3 to 30 (e.g., trimethylsilyl, triethylsilyl, triisopropylsilyl, tert-butyldimethylsilyl, phenyldimethylsilyl).

[Ring R]

The ring R includes an aromatic or non-aromatic hydrocarbon ring, a heterocyclic ring, and a polycyclic condensed ring formed by further combining these rings. Examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring and a phenazine ring.

[Photoelectric Conversion Device]

The photoelectric conversion device of the present invention comprises an electrically conductive film, an organic photoelectric conversion film and a transparent electrically conductive film. In a preferred embodiment, the photoelectric conversion device has an electron blocking layer, in addition to an electrically conductive film, an organic photoelectric conversion film and a transparent electrically conductive film, and this embodiment includes an embodiment where the electrically conductive film, the electron blocking film, the organic photoelectric conversion film and the transparent electrically conductive film are stacked in this order, and an embodiment where the electrically conductive film, the organic photoelectric conversion film, the electron blocking film and the transparent electrically conductive film are stacked in this order.

The organic photoelectric conversion film contains a compound represented by the following formula (1) and an n-type semiconductor.

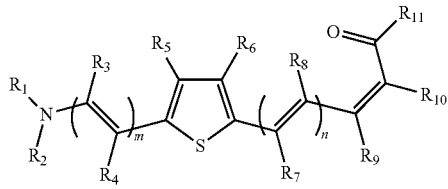

Formula (1)

wherein each of $R_1$ and $R_2$ independently represents a substituted aryl group, an unsubstituted aryl group, a substituted heteroaryl group or an unsubstituted heteroaryl group, each of $R_3$ to $R_{11}$ independently represents a hydrogen atom or a substituent provided that an acidic group is excluded, m represents 0 or 1, n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, or $R_{10}$ and $R_{11}$ may be combined with each other to form a ring, and when n is an integer of 2 or more, out of a plurality of $R_7$'s and $R_8$'s, a pair of $R_7$'s, a pair of $R_8$'s, or a pair of $R_7$ and $R_8$ may be combined with each other to form a ring.

The photoelectric conversion device of the present invention contains a compound represented by formula (1) and an n-type organic semiconductor in the photoelectric conversion film, whereby a device with high photoelectric conversion efficiency is obtained. The operation mechanism thereof is not clearly know, but it is presumed that thanks to a high molar extinction coefficient of the compound and production of a highly efficient charge separation state or highly efficient charge transport path by the formation of a bulk heterojunction structure with an n-type organic semiconductor (preferably a fullerene or a fullerene derivative), the photoelectric conversion efficiency can be enhanced.

Preferred embodiments of the photoelectric conversion device according to the present invention are described below.

Figure 1B:
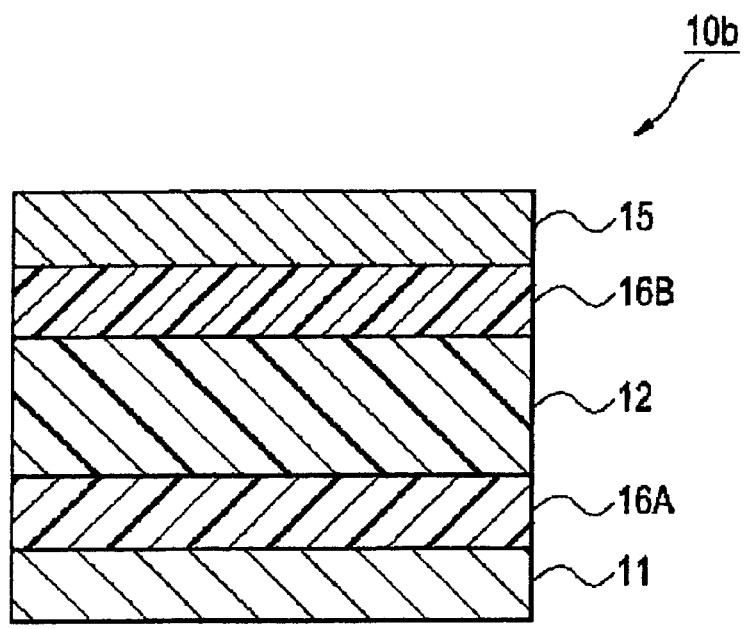

FIGS. 1A and 1B shows a configuration example of the photoelectric conversion device of the present invention.

The photoelectric conversion device 10a shown in FIG. 1A has a configuration where an electrically conductive film (hereinafter referred to as a lower electrode) 11 functioning as a lower electrode, an electron blocking layer 16A (electron blocking film) formed on the lower electrode 11, a photoelectric conversion layer 12 (organic photoelectric conversion film) formed on the electron blocking layer 16A, and a transparent electrically conductive film (hereinafter referred to as an upper electrode) 15 functioning as an upper electrode are stacked.

FIG. 1B shows another configuration example of the photoelectric conversion device. The photoelectric conversion device 10b shown in FIG. 1B has a configuration where an electron blocking layer 16A (electron blocking film), a photoelectric conversion layer 12 (organic photoelectric conversion film), a hole blocking layer 16B and an upper electrode 15 are stacked in this order on a lower electrode 11. Incidentally, in FIG. 1A and FIG. 1B, the order of stacking an electron blocking layer, a photoelectric conversion layer and a hole blocking layer may be reversed according to usage or properties.

In these cases, light is preferably incident on the organic photoelectric conversion film from above the upper electrode (transparent electrically conductive film).

Also, in using such a photoelectric conversion device, an electric field can be applied. In this case, the electrically conductive film and the transparent electrically conductive film define a pair of electrodes, and an electric field of, for example, $1 \times 10^{-4}$ to $1 \times 10^7$ V/cm can be applied between the pair of electrodes.

The elements constituting the photoelectric conversion device according to this embodiment are described below.

(Electrode)

Each of the electrodes (the upper electrode (transparent electrically conductive film) 15 and the lower electrode (electrically conductive film) 11) is composed of an electrically conductive material. Examples of the electrically conductive material which can be used include a metal, an alloy, a metal oxide, an electroconductive compound, and a mixture thereof.

Light is incident from the upper electrode 15 and therefore, the upper electrode 15 needs to be sufficiently transparent to light that is to be detected. Specific examples thereof include an electrically conductive metal oxide such as tin oxide doped with antimony or fluorine (ATO, FTO), tin oxide, zinc oxide, indium oxide, indium tin oxide (ITO) and indium zinc oxide (IZO); a thin metal film such as gold, silver, chromium and nickel; a mixture or laminate of such a metal and such an electrically conductive metal oxide; an inorganic electrically conductive substance such as copper iodide and copper sulfide; an organic electrically conductive material such as polyaniline, polythiophene and polypyrrole; and a laminate of such a material and ITO. Among these, an electrically conductive metal oxide is preferred in view of high electrical conductivity, transparency and the like. The upper electrode 15 is deposited on the organic photoelectric conversion layer 12 and therefore, is preferably deposited by a method causing no deterioration of the properties of the organic photoelectric conversion layer 12. Also, the upper electrode 15 is preferably composed of a transparent electrically conductive oxide.

The lower electrode 11 includes, according to usage, a case where transparency is imparted, a case where, conversely, a material capable of reflecting light is used without imparting transparency, and the like. Specific examples thereof include an electrically conductive metal oxide such as tin oxide doped with antimony or fluorine (ATO, FTO), tin oxide, zinc oxide, indium oxide, indium tin oxide (ITO) and indium zinc oxide (IZO); a metal such as gold, silver, chromium, nickel, titanium, tungsten and aluminum; an electrically conductive compound such as oxide and nitride of the metal (for example, titanium nitride (TiN)); a mixture or laminate of such a metal and such an electrically conductive metal oxide; an inorganic electrically conductive substance such as copper iodide and copper sulfide; an organic electrically conductive material such as polyaniline, polythiophene and polypyrrole; and a laminate of such a material and ITO or titanium nitride.

The method for forming the electrode is not particularly limited and may be appropriately selected by taking into consideration the aptitude for the electrode material. Specifically, the electrode can be formed, for example, by a wet system such as printing and coating, a physical system such as vacuum deposition, sputtering and ion plating, or a chemical system such as CVD and plasma CVD.

In the case where the material of the electrode is ITO, the electrode can be formed by a method such as electron beam method, sputtering method, resistance heating deposition method, chemical reaction method (e.g., sol-gel method) and coating of a dispersion of indium tin oxide. The film produced using ITO may be further subjected to, for example, a UV-ozone treatment or a plasma treatment. In the case where the material of the electrode is TiN, various methods including a reactive sputtering method are used, and the film formed can be further subjected to a UV-ozone treatment, a plasma treatment or the like.

The upper electrode 15 is preferably produced in a plasma-free state. When the upper electrode 15 is produced in a plasma-free state, the effect of plasma on the substrate can be reduced and good photoelectric conversion properties can be obtained. Here, the plasma-free state means a state where plasma is not generated during deposition of the upper electrode 15 or where the distance from a plasma source to the substrate is 2 cm or more, preferably 10 cm or more, more preferably 20 cm or more, and the amount of plasma reaching the substrate is reduced.

Examples of the apparatus generating no plasma during deposition of the upper electrode 15 include an electron beam deposition apparatus (EB deposition apparatus) and a pulsed laser deposition apparatus. As for the EB deposition apparatus or pulsed laser deposition apparatus, apparatuses described, for example, in Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*New Development of Transparent Conductive Film II*), CMC (2002), *Tomei Doden Maku no Gijutsu* (*Technology of Transparent Conductive Film*), JSPS, Ohmsha (1999), and references cited therein can be used. In the following, the method of depositing the transparent electrode film by using an EB deposition apparatus is referred to as an EB deposition method, and the method of depositing the transparent electrode film by using a pulsed laser deposition apparatus is referred to as a pulsed laser deposition method.

As for the apparatus capable of realizing a state where the distance from a plasma source to the substrate is 2 cm or more and the amount of plasma reaching the substrate is reduced (hereinafter referred to as a "plasma-free deposition apparatus"), an opposed-target sputtering apparatus, an arc plasma deposition method and the like are considered, and examples of such an apparatuses which can be used include those described in Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*Development of Transparent Conductive Film II*), CMC (2002), *Tomei Doden Maku no Gijutsu* (*Technology of Transparent Conductive Film*), JSPS, Ohmsha (1999), and references cited therein.

In the case where the upper electrode 15 is a transparent electrically conductive film such as TCO, a DC short or an increase of leak current sometimes occurs. One of causes thereof is considered because fine cracks introduced into the photoelectric conversion layer 12 are coveraged by a dense film such as TCO to increase the conduction with the first electrode film 11 on the opposite side. Therefore, in the case of an electrode having relatively poor film quality such as Al, the leak current hardly increases. The increase of leak current can be greatly suppressed by controlling the film thickness of the upper electrode 15 with respect to the film thickness (that is, the crack depth) of the photoelectric conversion layer 12. The thickness of the upper electrode 15 is preferably ⅕ or less, more preferably ¹⁄₁₀ or less, of the thickness of the photoelectric conversion layer 12.

Usually, when the thickness of the electrically conductive film is made smaller than a certain range, an abrupt increase of the resistance value is incurred, but in the solid-state imaging device where the photoelectric conversion device according to this embodiment is incorporated, the sheet resistance may be, preferably, from 100 to 10,000 Ω/sq. and the latitude as to in which range the film thickness can be reduced is large. Also, as the thickness of the upper electrode (transparent electrically conductive film) 15 is smaller, the quantity of light absorbed is reduced and the light transmittance is generally increased. The increase of light transmittance brings about an increase of light absorption in the photoelectric conversion layer 12 and an increase of photoelectric conversion performance, and this is very preferred. Considering the suppression of leak current and the increase of resistance value of thin film as well as the increase of transmittance, which are associated with reduction in the film thickness, the thickness of the upper electrode 15 is preferably from 5 to 100 nm, more preferably from 5 to 20 nm.

(Photoelectric Conversion Layer)

The photoelectric conversion layer contains a compound represented by the following formula (1):

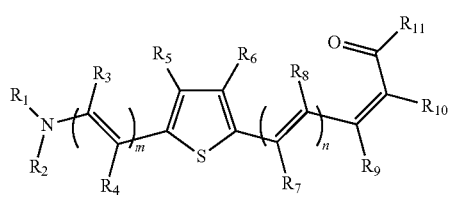

Formula (1)

wherein each of $R_1$ and $R_2$ independently represents a substituted aryl group, an unsubstituted aryl group, a substituted heteroaryl group or an unsubstituted heteroaryl group, each of $R_3$ to $R_{11}$ independently represents a hydrogen atom or a substituent provided that an acidic group is excluded, m represents 0 or 1, n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, or $R_{10}$ and $R_{11}$ may combine with each other to form a ring, and when n is an integer of 2 or more, out of a plurality of $R_7$'s and $R_8$'s, a pair of $R_7$'s, a pair of $R_8$'s, or a pair of $R_7$ and $R_8$ may combine with each other to form a ring.

m represents 0 or 1 and is preferably 0.

n represents an integer of 0 or more and preferably represents any integer of 0 to 3. When n becomes large, the absorption wavelength region is allowed to reside on a long wavelength side, but from the standpoint of having appropriate absorption in the visible region, n is more preferably 0, 1 or 2.

Each of $R_1$ and $R_2$ independently represents a substituted or unsubstituted aryl group or a substituted or unsubstituted heteroaryl group.

The aryl group represented by $R_1$ and $R_2$ is preferably an aryl group having a carbon number of 6 to 30, more preferably an aryl group having a carbon number of 6 to 20. Specific examples of the aryl group include a phenyl group, a naphthyl group, a biphenylyl group, a terphenyl group, an anthryl group and a fluorenyl group.

The substituent of the substituted aryl group in $R_1$ and $R_2$ is preferably an alkyl group (e.g., methyl, ethyl, tert-butyl), an alkoxy group (e.g., methoxy, ethoxy, isopropoxy), an aryl group (e.g., phenyl, naphthyl, phenanthryl, anthryl) or a heteroaryl group (e.g., thienyl, furanyl, pyridyl, carbazolyl).

The aryl group or substituted aryl group represented by $R_1$ and $R_2$ is preferably a phenyl group, an alkyl-substituted phenyl group, a biphenyl group, a naphthyl group, a phenanthryl group, an anthryl group or a substituted fluorenyl group (preferably a 9,9'-dimethyl-2-fluorenyl group).

In the case where each of $R_1$ and $R_2$ is a heteroaryl group, the heteroaryl group is preferably a heteroaryl group composed of a 5-, 6- or 7-membered ring or a condensed ring thereof. Examples of the heteroatom contained in the heteroaryl group include an oxygen atom, a sulfur atom and a nitrogen atom. Specific examples of the ring constituting the heteroaryl group include a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazane ring, a tetrazole ring, a pyrane ring, a thiine ring, a pyridine ring, a piperidine ring, an oxazine ring, a morpholine ring, a thiazine ring, a pyridazine ring, a pyrimidine ring, a pyrazine ring, a piperazine ring and a triazine ring.

Examples of the condensed ring include a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a carbazole ring, a xanthene ring, an acridine ring, a phenanthridine ring, a phenanthroline ring, a phenazine ring, a phenoxazine ring, a thianthrene ring, an indolizine ring, a quinolidine ring, a quinuclidine ring, a naphthylidine ring, a purine ring and a pteridine ring.

The substituent of the substituted heteroaryl group in $R_1$ and $R_2$ is preferably an alkyl group (e.g., methyl, ethyl, tert-butyl), an alkoxy group (e.g., methoxy, ethoxy, isopropoxy), an aryl group (e.g., phenyl, naphthyl, phenanthryl, anthryl) or a heteroaryl group (e.g., thienyl, furanyl, pyridyl, carbazolyl).

The heteroaryl group or substituted heteroaryl group represented by $R_1$ and $R_2$ is preferably a thienyl group, a substituted thienyl group, a furanyl group or a carbazolyl group.

Each of $R_1$ and $R_2$ is preferably a substituted or unsubstituted phenyl group, a substituted or unsubstituted naphthyl group, a substituted or unsubstituted biphenyl group, a substituted or unsubstituted anthryl group, a substituted or unsubstituted fluorenyl group, or a group composed of a ring selected from a furan ring, a thiophene ring, a benzofuran ring, an isobenzofuran ring, a benzothiophene ring and a carbazole ring.

In formula (1), each of $R_3$ to $R_{11}$ independently represents a hydrogen atom or a substituent provided that an acidic group is excluded. In the case where each of $R_3$ to $R_{11}$ represents a substituent, examples of the substituent include the substituent W. The substituent represented by $R_3$ to $R_{11}$ is preferably a halogen atom, an alkyl group, an alkenyl group, an alkynyl group, a cycloalkyl group, an alkoxy group, an alkylcarbonyl group, an alkylthio group, an aryl group, a heteroaryl group or a mercapto group, more preferably a halogen atom (e.g., fluorine, chlorine, bromine, iodine), an alkyl group having a carbon number of 1 to 20 (preferably a carbon number of 1 to 10), an alkenyl group having a carbon number of 2 to 20 (preferably a carbon number of 2 to 10), an alkynyl group having a carbon number of 2 to 20 (preferably a carbon number of 2 to 10), a cycloalkyl group having a carbon number of 3 to 8 (preferably a carbon number of 4 to 6), an alkoxy group having a carbon number of 1 to 20 (preferably a carbon number of 1 to 10), an alkylthio group having a carbon number of 1 to 20 (preferably a carbon number of 1 to 10), an aryl group having a carbon number of 6 to 30 (preferably a carbon number of 6 to 20), a heteroaryl group composed of a 5-, 6- or 7-membered ring or a condensed ring thereof, containing at least any one of oxygen atom, sulfur atom and nitrogen atom as a heteroatom, or a mercapto group.

The above-described alkyl group, alkenyl group and alkynyl group may be either branched or linear.

In the case where each of $R_3$ to $R_8$ is a substituent, the substituent is more preferably an alkyl group having a carbon number of 1 to 10, an alkenyl group having a carbon number of 2 to 10, an alkoxy group having a carbon number of 1 to 10, or an alkylthio group having a carbon number of 1 to 10.

Specifically, the alkyl group is preferably a methyl group, an ethyl group, a propyl group, an i-propyl group or a tert-butyl group.

The alkenyl group is preferably a vinyl group ($CH_2=CH-$) or an allyl group ($CH_2=CHCH_2-$).

In the case where $R_9$ is a substituent, the substituent is more preferably an alkyl group having a carbon number of 1 to 10.

$R_9$ is preferably a hydrogen atom, a methyl group or an ethyl group, more preferably a hydrogen atom.

In the case where each of $R_3$ to $R_{11}$ represents a substituent, the substituent may have a further substituent. Examples of the further substituent include the substituent W. Among these, a halogen atom, an alkyl group (preferably having a carbon number of 1 to 6), and an aryl group (preferably having a carbon number of 6 to 10) are preferred.

$R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, or $R_{10}$ and $R_{11}$ may combine with each other to form a ring, and when n is an integer of 2 or more, out of a plurality of $R_7$'s and $R_8$'s, a pair of $R_7$'s, a pair of $R_8$'s, or a pair of $R_7$ and $R_8$ may combine with each other to form a ring.

Examples of the ring formed include the ring R. Preferred examples include, but are not limited to, the followings. Also, the followings can be used in any combination.

- A case where $R_1$ and $R_2$ are combined to form a carbazole ring together with the nitrogen atom to which $R_1$ and $R_2$ are bonded.
- A case where $R_5$ and $R_6$ are combined to form a benzene ring or a dioxane ring (in this case, the ring combines with the thiophene ring formed by combining $R_5$ and $R_6$, to form a 3,4-ethylenedioxythiophene ring).
- A case where m is 1 or more and where $R_3$ and $R_5$ are combined to form a benzene ring or where either $R_3$ or $R_5$ is a sulfur atom-containing group and these members are combined to form a thiophene ring.
- A case where n is 1 or more and where $R_6$ and $R_8$ are combined to form a benzene ring or where either $R_6$ or $R_8$ is a sulfur atom-containing group and these members are combined to form a thiophene ring.
- A case where m is 2 or more and where a pair of $R_3$ and $R_5$ and a pair of $R_3$ and $R_3'$ each is combined to form a naphthalene ring or where either $R_3$ or $R_5$ and either $R_3$ or $R_3'$ are a sulfur atom-containing group and each pair is combined to form a benzothiophene ring.
- A case where n is 2 or more and where a pair of $R_6$ and $R_8$ and a pair of $R_8$ and $R_8'$ each is combined to form a naphthalene ring or where either $R_6$ or $R_8$ and either $R_8$ or $R_8'$ are a sulfur atom-containing group and each pair is combined to form a benzothiophene ring.

Examples of the ring formed by $R_{10}$ and $R_{11}$ include 1,3-indandione, 1,3-benzindandione, 1,3-cyclohexanedione, 5,5-dimethyl-1,3-cyclohexanedione, 1,3-dioxane-4,6-dione, 1-phenyl-2-pyrazolin-5-one, 3-methyl-1-phenyl-2-pyrazolin-5-one, 1-(2-benzothiazoyl)-3-methyl-2-pyrazolin-5-one and pyrimidine-2,4,6-trione.

The compound represented by formula (1) is preferably a compound represented by the following formula (2).

Formula (2)

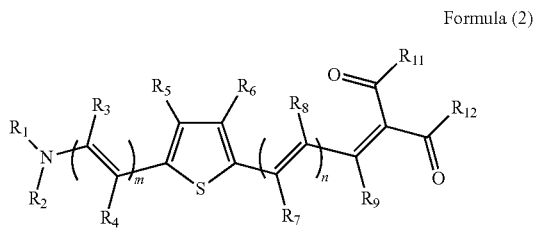

wherein $R_1$ to $R_9$, m and n have the same meanings as above, each of $R_{11}$ and $R_{12}$ independently represents a hydrogen atom or a substituent, and $R_{11}$ and $R_{12}$ may combine with each other to form a ring.

In the case of forming a ring by $R_{11}$ and $R_{12}$, examples of the ring include those of the ring formed by $R_{10}$ and $R_{11}$.

The compound represented by formula (2) is preferably a compound represented by the following formula (3).

Formula (3)

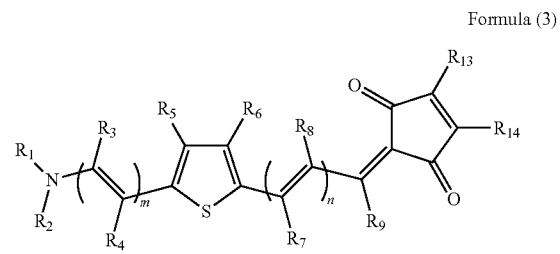

wherein $R_1$ to $R_9$, m and n have the same meanings as above, each of $R_{13}$ and $R_{14}$ independently represents a hydrogen atom or a substituent, and $R_{13}$ and $R_{14}$ may combine with each other to form a ring.

In the case of forming a ring by $R_{13}$ and $R_{14}$, examples of the ring include the ring R. Among these, a benzene ring, a naphthalene ring and an anthracene ring are preferred.

The compound represented by formula (3) is preferably a compound represented by the following formula (4) or a compound represented by the following formula (5).

Formula (4)

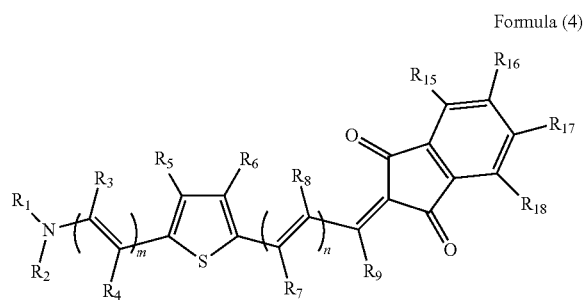

(wherein $R_1$ to $R_9$, m and n have the same meanings as above, each of $R_{15}$ to $R_{18}$ independently represents a hydrogen atom or a substituent, and $R_{15}$ and $R_{16}$, $R_{16}$ and $R_{17}$, or $R_{17}$ and $R_{18}$ may be combined with each other to form a ring).

Formula (5)

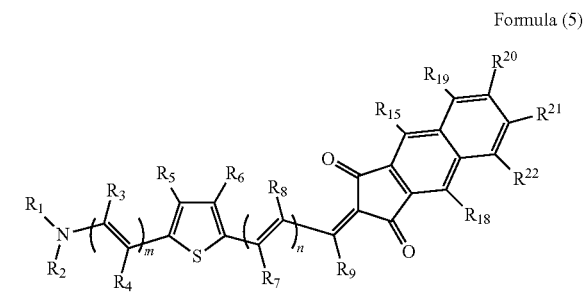

(wherein $R_1$ to $R_9$, m and n have the same meanings as above, each of $R_{15}$ and $R_{18}$ to $R_{22}$ independently represents a hydrogen atom or a substituent, and $R_{15}$ and $R_{19}$, $R_{19}$ and $R_{20}$, $R_{20}$ and $R_{21}$, $R_{21}$ and $R_{22}$, or $R_{22}$ and $R_{18}$ may be combined with each other to form a ring).

In formulae (4) and (5), each of $R_{15}$ to $R_{22}$ is preferably a hydrogen atom, a halogen atom, an alkyl group having a carbon number of 1 to 10, an aryl group having a carbon number of 6 to 20, or a heteroaryl group composed of a 5-, 6- or 7-membered ring or a condensed ring thereof, containing at least any one of oxygen atom, sulfur atom and nitrogen atom as a heteroatom, more preferably a hydrogen atom, a fluorine atom, an alkyl group having a carbon number of 1 to 10, or an aryl group having a carbon number of 6 to 20.

The compound represented by formula (4) and the compound represented by formula (5) are novel compounds not found in literatures and are useful particularly as a photoelectric conversion material used in photosensors and photocells. Also, as other applications, the compounds can be used, for example, as a coloring material, a liquid crystal material, an organic semiconductor material, an organic luminescence device material, a charge transport material, a medical material, and a fluorescent diagnostic agent material.

The compounds represented by formulae (1) to (5) can be synthesized, for example, according to the following reactions (when the starting material dibromothiophene derivative is symmetric).

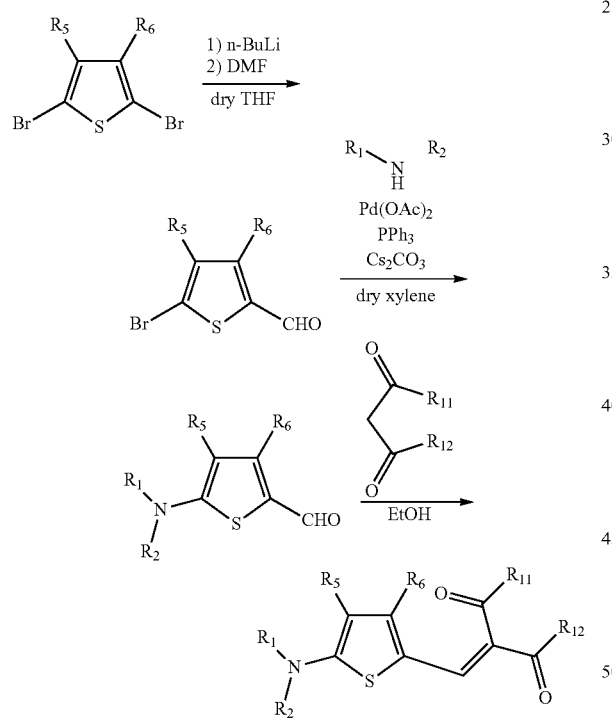

Each reaction above can be performed by referring to a known synthesis technique. The synthesis of an aldehyde form from a bromo form can be performed by referring to *J. Org. Chem.*, 2000, 65, 9120. The reaction with amine is known as a Buchwald-Hartwig reaction (see, *Org. Synth.*, 2004, 10, 423, and *Org. Synth.*, 2002, 78, 23). The reaction of an aldehyde form and 1,3-diketone is known as Knoevenagel condensation reaction (see, *Ber. Deutsch. Chem. Ges.*, 1898, 31, 2596). The reaction of an aldehyde form and a monoketone is known as aldol condensation reaction (see, *J. Am. Chem. Soc.*, 1979, 101, 1284).

In the case where the starting material is asymmetric (when $m \geq 1$ and $n=0$), the compounds can be synthesized according to the following reaction.

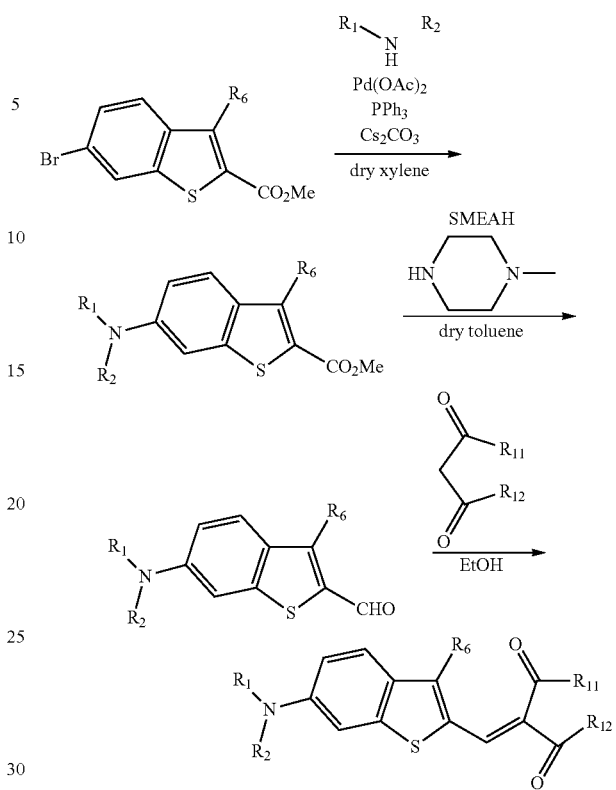

SMEAH: Sodium bis(2-methoxyethoxy)aluminum hydride

The starting compound can be synthesized according to the method described in *J. Med. Chem.*, 2007, 50, 4793. The reduction reaction from an ester form to an aldehyde form can be performed by referring to *Synthesis*, 2003, 822.

Furthermore, when $m=0$ and $n \geq 1$ the compounds can be synthesized according to the following reaction.

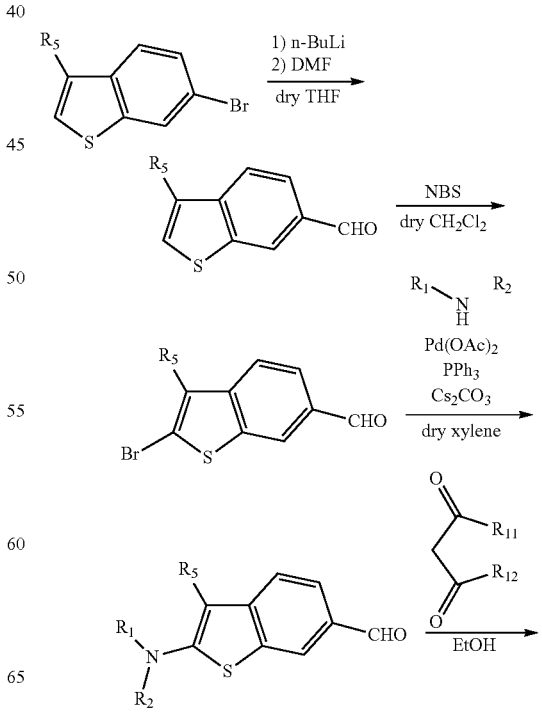

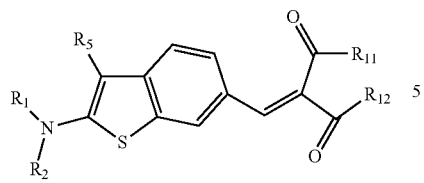

The starting compound can be synthesized by the method described in *J. Med. Chem.*, 2003, 46, 2446. The bromination using NBS (N-bromosuccinimide) can be performed by referring to *Tetrahedron*, 2001, 17, 3785.

Also, when n is 2 or more and a ring is formed by $R_7$ and $R_8'$, the compounds can be synthesized according to the following reaction.

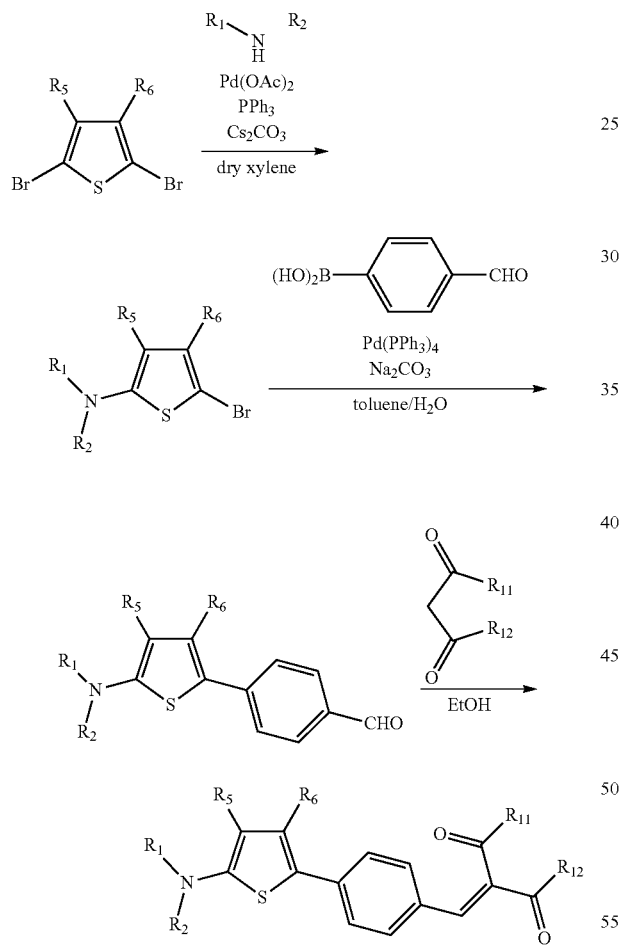

The coupling reaction of a bromo form and boric acid is known as Suzuki-Miyaura coupling reaction (see, *Tetrahedron Lett.*, 1979, 3437).

In the formulae, $R_1$, $R_2$, $R_5$, $R_6$, $R_{11}$ and $R_{12}$ have the same meanings as above.

The compound represented by formula (5) is preferably a compound represented by the following formula (11) or the following formula (12).

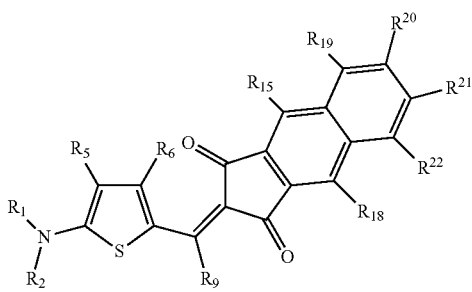

wherein $R_1$, $R_2$, $R_5$, $R_6$, $R_9$, $R_{15}$ and $R_{18}$ to $R_{22}$ have the same meanings as above, and preferred ranges are also the same.

Formula (12)

wherein $R_1$, $R_2$, $R_5$, $R_7$, $R_9$, $R_{15}$ and $R_{18}$ to $R_{22}$ have the same meanings as above, and preferred ranges are also the same.

(Molecular Weight)

In view of suitability for film production, the molecular weight of the compounds represented by formula (1) is preferably from 300 to 1,500, more preferably from 350 to 1,200, still more preferably from 400 to 900. If the molecular weight is too small, the thickness of the photoelectric conversion film deposited is reduced due to volatilization, whereas if the molecular weight is excessively large, the compound cannot be vapor-deposited and a photoelectric conversion device cannot be fabricated.

(Melting Point)

In view of deposition stability, the melting point of the compound represented by formula (1) is preferably 200° C. or more, more preferably 250° C. or more, still more preferably 280° C. or more. If the melting point is low, the compound melts out before vapor deposition, making it impossible to stably deposit a film, and in addition, the decomposition product of the compound increases to deteriorate the photoelectric conversion performance.

(Absorption Spectrum)

From the standpoint of broadly absorbing light in the visible region, the peak wavelength in the absorption spectrum of the compound represented by formula (1) is preferably from 450 to 700 nm, more preferably from 480 to 700 nm, still more preferably from 510 to 680 nm.

(Molar Extinction Coefficient of Peak Wavelength)

From the standpoint of efficiently utilizing light, the molar extinction coefficient of the compound represented by formula (1) is preferably higher and is preferably 30,000 $M^{-1}$ $cm^{-1}$ or more, more preferably 50,000 $M^{-1}$ $cm^{-1}$ or more, still more preferably 70,000 $M^{-1}$ $cm^{-1}$ or more.

Specific examples of the compound represented by formula (1) are illustrated below, but the present invention is not limited thereto.

(1)

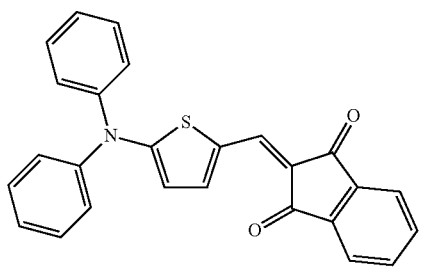

(2)

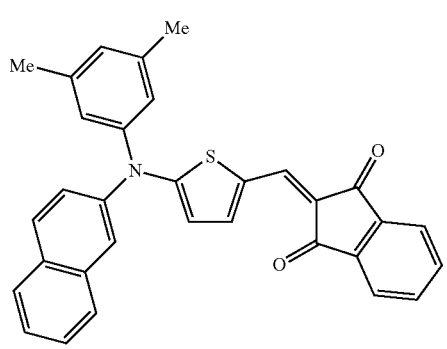

(3)

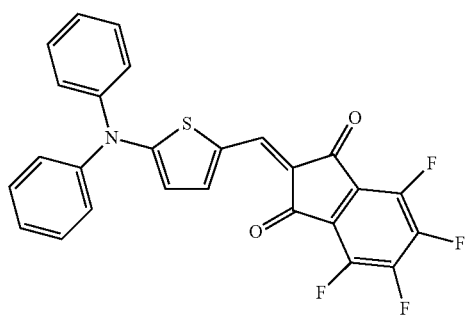

(4)

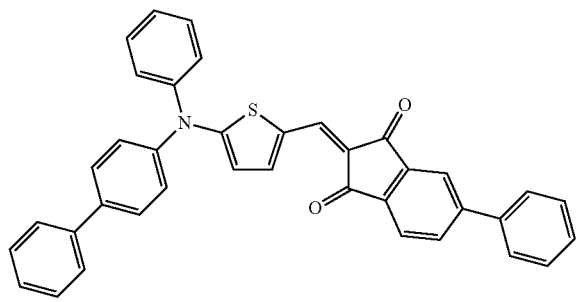

(5)

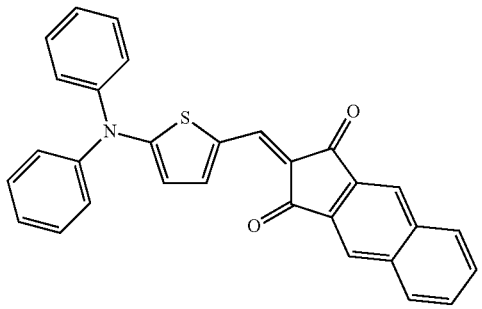

(6)

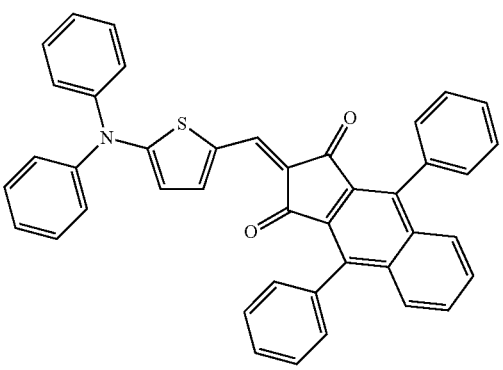

(7)

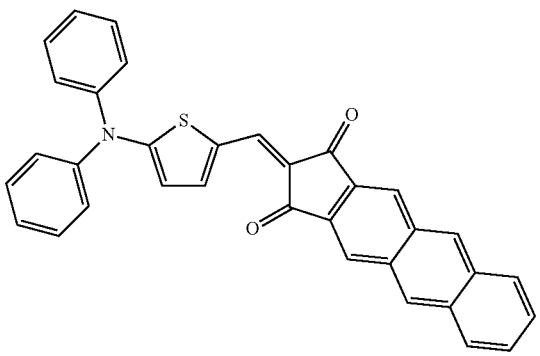

(8)

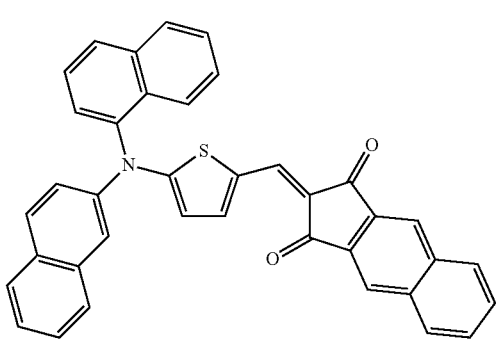

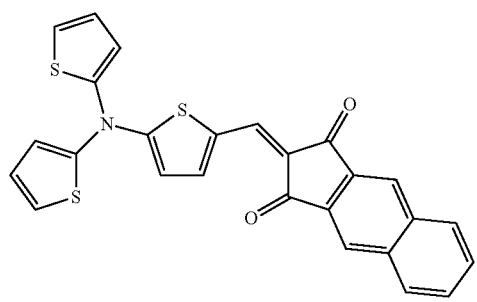
(9)
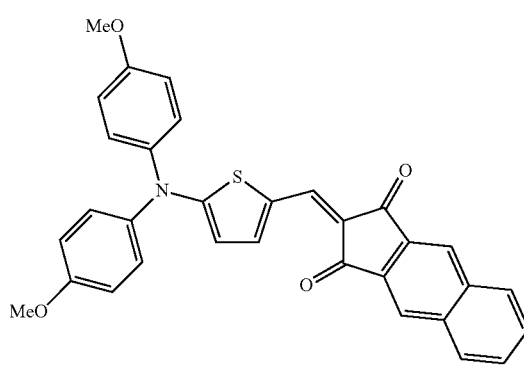
(10)
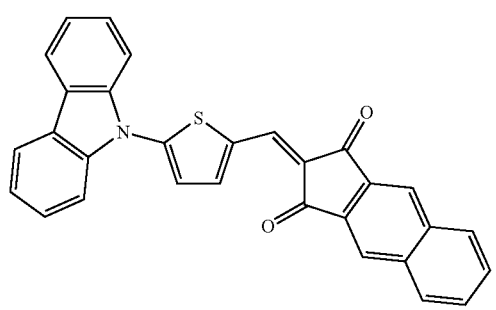
(11)
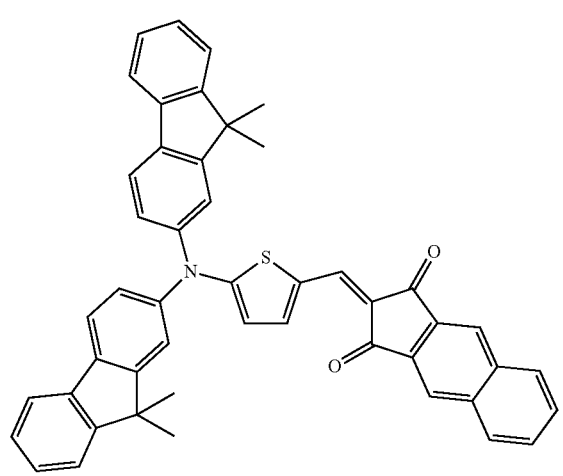
(12)
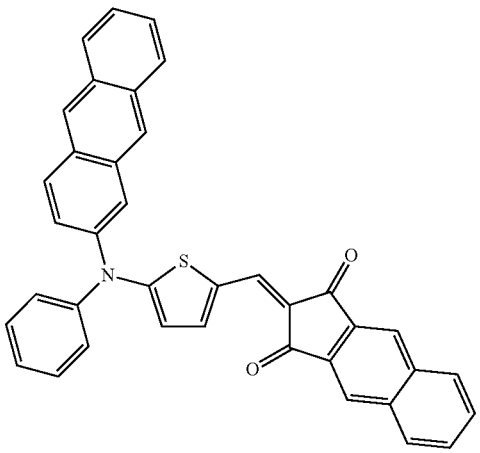
(13)
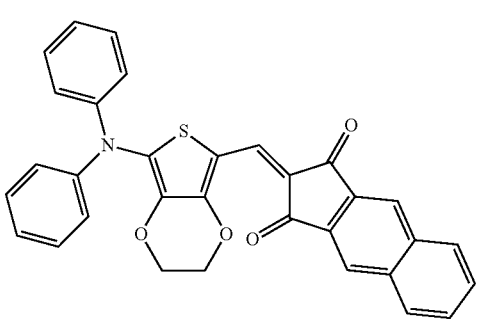
(14)
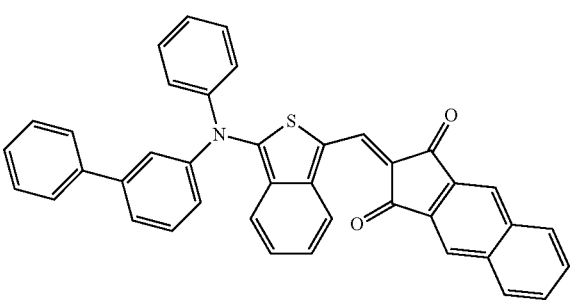
(15)
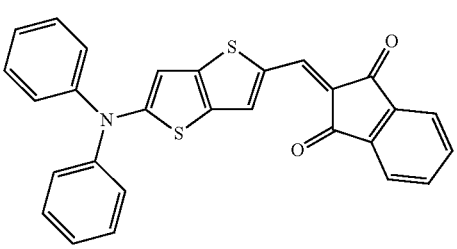
(16)

(17)
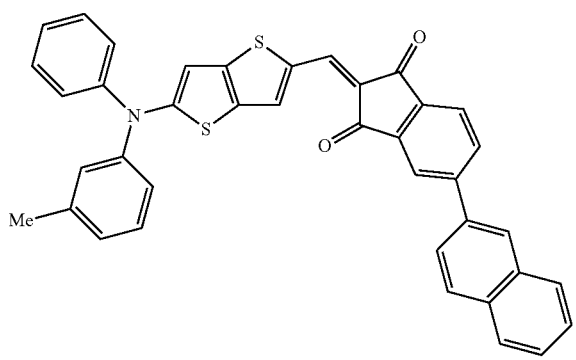
(18)
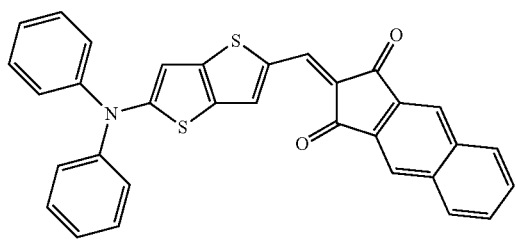
(19)
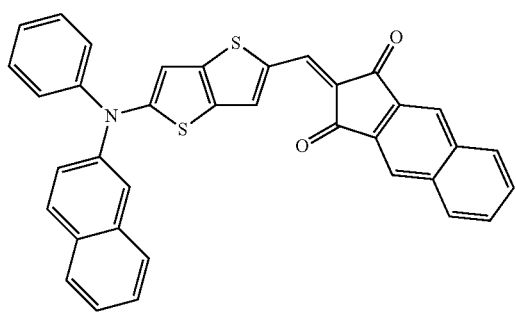
(20)
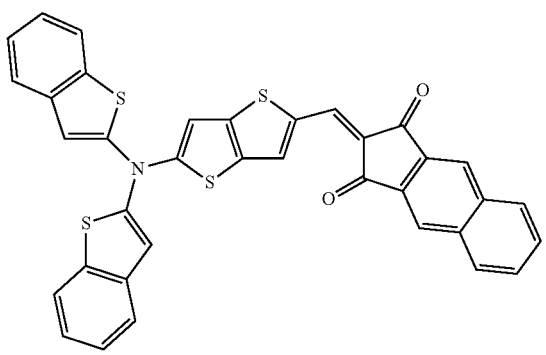
(21)
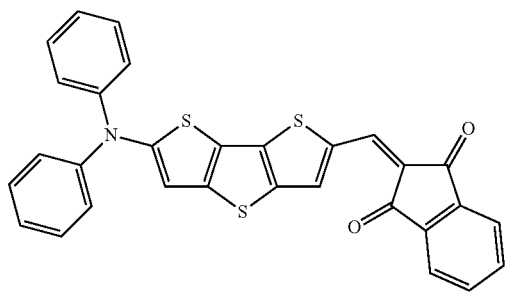
(22)
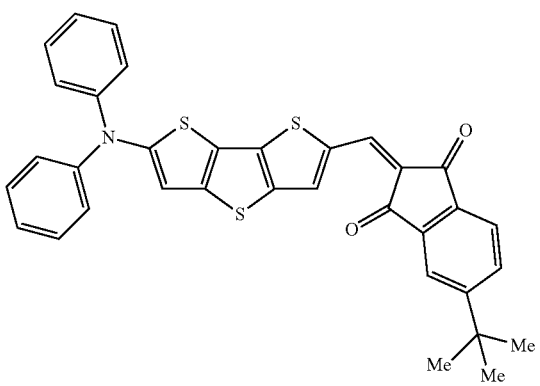
(23)
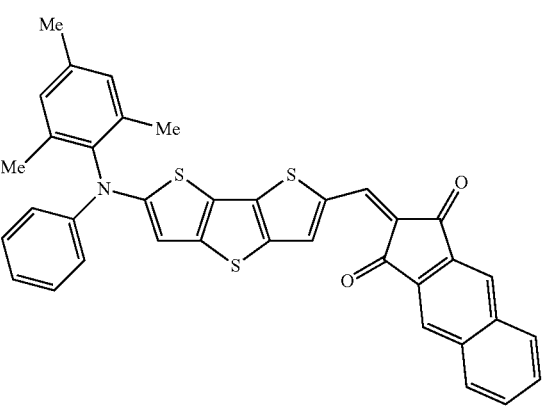
(24)
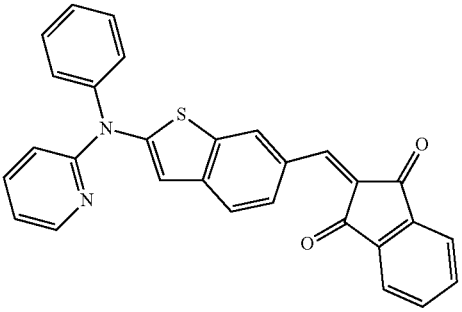

-continued
(25)
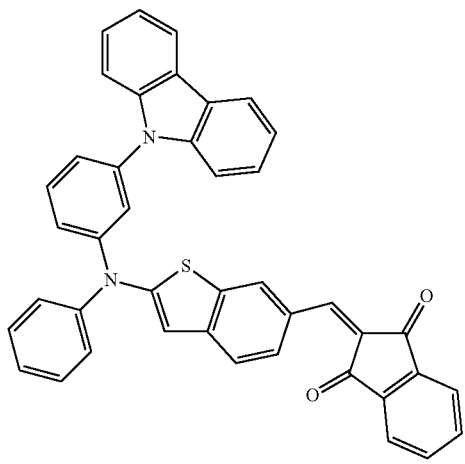
(26)
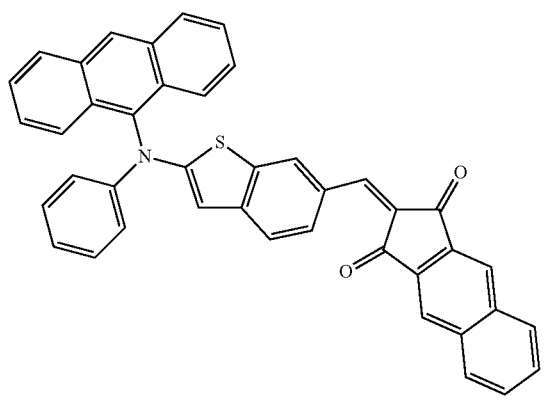
(27)
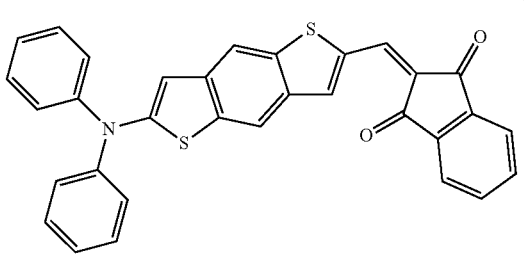
(28)
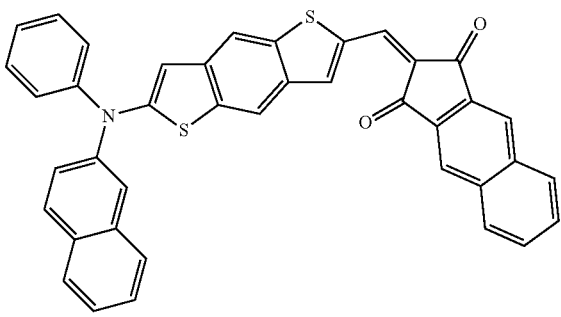
-continued
(29)
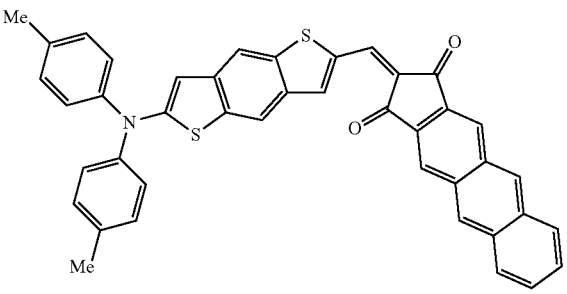
(30)
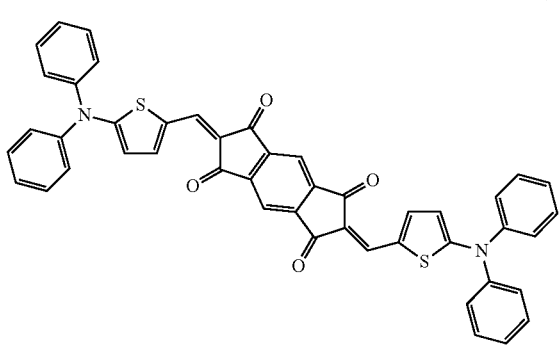
(31)
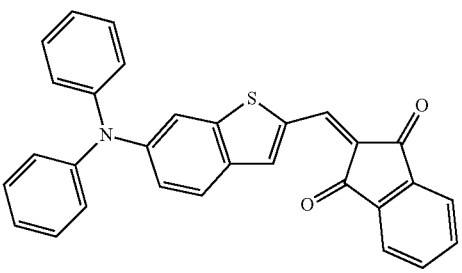
(32)
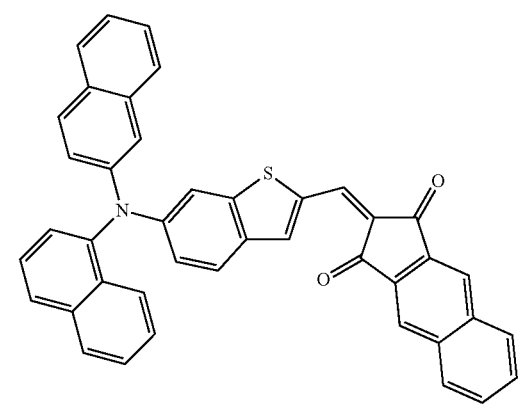

(33)

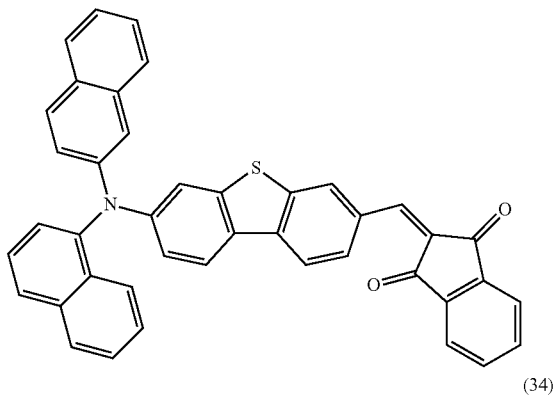

(34)

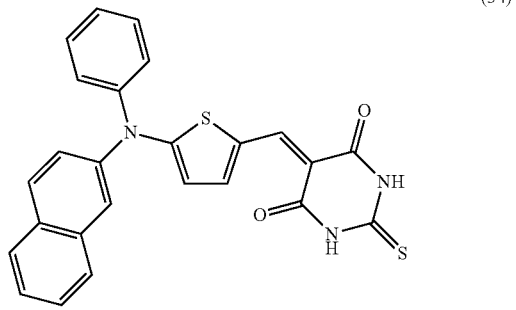

(35)

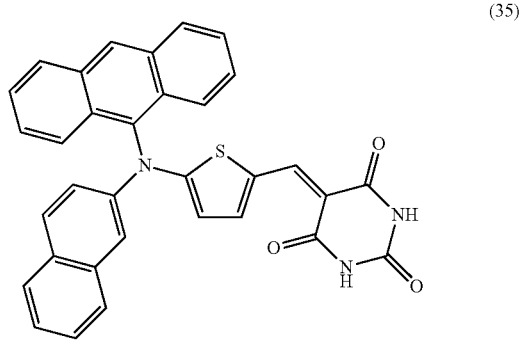

(36)

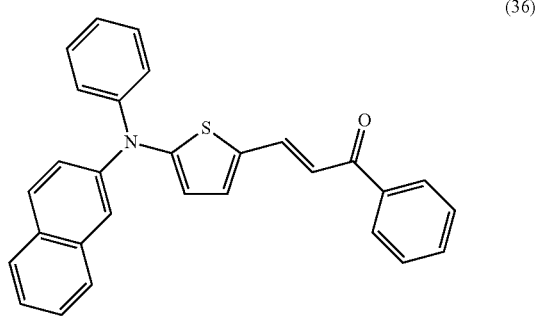

(37)

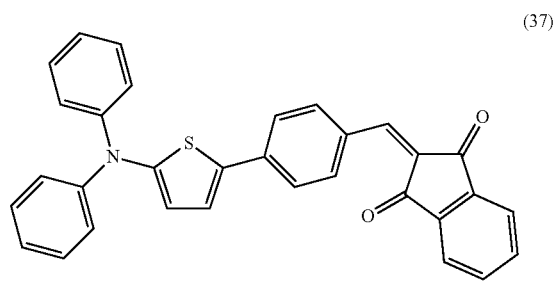 [SMILES: O=C1C(=Cc2ccc(-c3ccc(N(c4ccccc4)c4ccccc4)s3)cc2)C(=O)c2ccccc21]

The photoelectric conversion layer 12 contains an n-type organic semiconductor.

The n-type organic semiconductor is an acceptor-type organic semiconductor and indicates an organic compound having a property of readily accepting an electron, mainly typified by an electron-transporting organic compound. More specifically, this is an organic compound having a larger electron affinity when two organic compounds are used in contact. Accordingly, for the acceptor-type organic compound, any organic compound can be used as long as it is an organic compound having an electron accepting property. Examples thereof include a fullerene derivative, a fused aromatic carbocyclic compound (a naphthalene derivative, an anthracene derivative, a phenanthrene derivative, a tetracene derivative, a pyrene derivative, a perylene derivative and a fluoranthene derivative), a 5- to 7-membered heterocyclic compound containing nitrogen atom, oxygen atom or sulfur atom (e.g., pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine), a polyarylene compound, a fluorene compound, a cyclopentadiene compound, a silyl compound, and a metal complex having a nitrogen-containing heterocyclic compound as a ligand.

The fullerene indicates fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene $C_{540}$, a mixed fullerene or a fullerene nanotube, and the fullerene derivative indicates a compound obtained by adding a substituent to such a fullerene. The substituent is preferably an alkyl group, an aryl group or a heterocyclic group.

The compounds described in JP-A-2007-123707 are preferred as the fullerene derivative.

As for the fullerene and fullerene derivative, the compounds described, for example, in *Kikan Kagaku Sosetsu (Scientific Review Quarterly)*, No. 43, edited by The Chemical Society of Japan (1999), JP-A-10-167994, JP-A-11-255508, JP-A-11-255509, JP-A-2002-241323 and JP-A-2003-196881 may also be used.

Out of a fullerene and a fullerene derivative, a fullerene is preferred, and fullerene $C_{60}$ is more preferred.

The photoelectric conversion layer preferably has a bulk heterojunction structure formed in a state of the compound represented by formula (1) and a fullerene or a fullerene derivative being mixed. The heterojunction structure contained therein compensates for a drawback that the carrier diffusion length in the photoelectric conversion layer is short, whereby the photoelectric conversion efficiency of the photoelectric conversion layer can be enhanced. Incidentally, the bulk heterojunction structure is described in detail, for example, in JP-A-2005-303266, paragraphs [0013] and [0014].

The volume ratio of the fullerene or fullerene derivative to the compound represented by formula (1) (fullerene or fullerene derivative/compound represented by formula (1)× 100(%)) is preferably 50% or more, more preferably from 80 to 1,000% (volume ratio), still more preferably from 100 to 700% (volume ratio).

The photoelectric conversion layer can be deposited by a dry deposition method or a wet deposition method. Specific examples of the dry deposition method include a physical vapor growth method such as vacuum deposition method, sputtering method, ion plating method and MBE method, and a CVD method such as plasma polymerization. As for the wet deposition method, a cast method, a spin coating method, a dipping method, an LB method and the like are used. A dry deposition method is preferred, and a vacuum deposition method is more preferred. In the case of depositing the layer by a vacuum deposition method, the production conditions such as vacuum degree and vapor deposition temperature can be set in accordance with conventional methods.

The thickness of the photoelectric conversion layer is preferably from 10 to 1,000 nm, more preferably from 50 to 800 nm, still more preferably from 100 to 500 nm. With a thickness of 10 nm or more, a suitable effect of suppressing a dark current is obtained, and with a thickness of 1,000 nm or less, a suitable photoelectric conversion efficiency is obtained.

(Electron Blocking Layer)

For the electron blocking layer, an electron-donating organic material can be used. Specifically, examples of the low molecular material which can be used include an aromatic diamine compound such as N,N-bis(3-methylphenyl)-(1,1'-biphenyl)-4,4'-diamine (TPD) and 4,4'-bis[N-(naphthyl)-N-phenylamino]biphenyl (α-NPD), oxazole, oxadiazole, triazole, imidazole, imidazolone, a stilbene derivative, a pyrazolone derivative, tetrahydroimidazole, a polyarylalkane, butadiene, 4,4',4"-tris(N-(3-methylphenyl) N-phenylamino)triphenylamine (m-MTDATA), a porphyrin compound such as porphin, copper tetraphenylporphin, phthalocyanine, copper phthalocyanine and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an anilamine derivative, an amino-substituted chalcone derivative, an oxazole derivative, a styrylanthracene derivative, a fluorenone derivative, a hydrazone derivative, and a silazane derivative. As for the polymer material, a polymer such as phenylenevinylene, fluorene, carbazole, indole, pyrene, pyrrole, picolin, thiophene, acetylene and diacetylene, or a derivative thereof may be used. A compound having a sufficient hole transportability may be used even if it is not an electron-donating compound.

Specifically, the compounds described in JP-A-2008-72090, paragraphs [0083] to are preferred.

(Hole Blocking Layer)

For the hole-blocking layer, an electron-accepting organic material can be used.

Examples of the electron-accepting material which can be used include an oxadiazole derivative such as 1,3-bis(4-tert-butylphenyl-1,3,4-oxadiazolyl)phenylene (OXD-7); an anthraquinodimethane derivative; a diphenylquinone derivative; a bathocuproine, a bathophenanthroline and a derivative thereof; a triazole compound; a tris(8-hydroxyquinolinato) aluminum complex; a bis(4-methyl-8-quinolinato)aluminum complex; a distyrylarylene derivative; and a silole compound. Also, a material having sufficient electron transportability may be used even if it is not an electron-accepting organic material. A porphyrin-based compound, a styryl-based compound such as DCM (4-dicyanomethylene-2-methyl-6-(4-(dimethylaminostyryl))-4H pyran), and a 4H pyran-based compound can be used. Specifically, the compounds described in JP-A-2008-72090, paragraphs [0073] to [0078] are preferred.

The thickness of the electron blocking layer/hole blocking layer is preferably from 10 to 200 nm, more preferably from 30 to 150 nm, still more preferably from 50 to 100 nm, because if this thickness is too small, the effect of suppressing a dark current is decreased, whereas if the thickness is excessively large, the photoelectric conversion efficiency is deteriorated.

[Photosensor]

The photoelectric conversion device is roughly classified into a photocell and a photo sensor, and the photoelectric conversion device of the present invention is suited for a photosensor. The photosensor may be a photosensor using the above-described photoelectric conversion device alone or may be in the mode of a line sensor where the photoelectric conversion devices are linearly arranged, or a two-dimensional sensor where the photoelectric conversion devices are arranged on a plane. The photoelectric conversion device of the present invention functions as an imaging device, in the line sensor, by converting the optical image information into electric signals with use of an optical system and a drive part like, for example, a scanner and, in the two-dimensional sensor, by forming an image of optical image information on a sensor by means of an optical system and converting it into electric signals like an imaging module.

The photocell is a power generating unit and therefore, the efficiency of converting light energy into electric energy is an important performance, but the dark current that is a current in a dark place does not become a problem in function. Furthermore, a heating step in the later stage, such as placement of a color filter, is not required. In the photosensor, high-precision conversion of light/dark signals into electric signals is an important performance and in turn, the efficiency of converting light quantity into a current is also an important performance. Moreover, a signal when output in a dark place works out to a noise and therefore, low dark current is required. Furthermore, the resistance to a step in the later sage is also important.

[Imaging Device]

Configuration examples of an imaging device equipped with the photoelectric conversion device are described below. In the following configuration examples, the members and the like having the same configuration/action as the members described above are indicated by the same or like symbols or numerical references in the figure, and their description is simplified or omitted.

The imaging device is a device of converting optical information of an image into electric signals, where a plurality of photoelectric conversion devices are arranged in the same plane on a matrix and where light signals can be converted into electric signals in each photoelectric conversion device (pixel) and each pixel can sequentially output the electric signals to the outside of the imaging device. Therefore, the imaging device has one photoelectric conversion device and one or more transistors per one pixel.

(First Configuration Example of Imaging Device)

Figure 2:
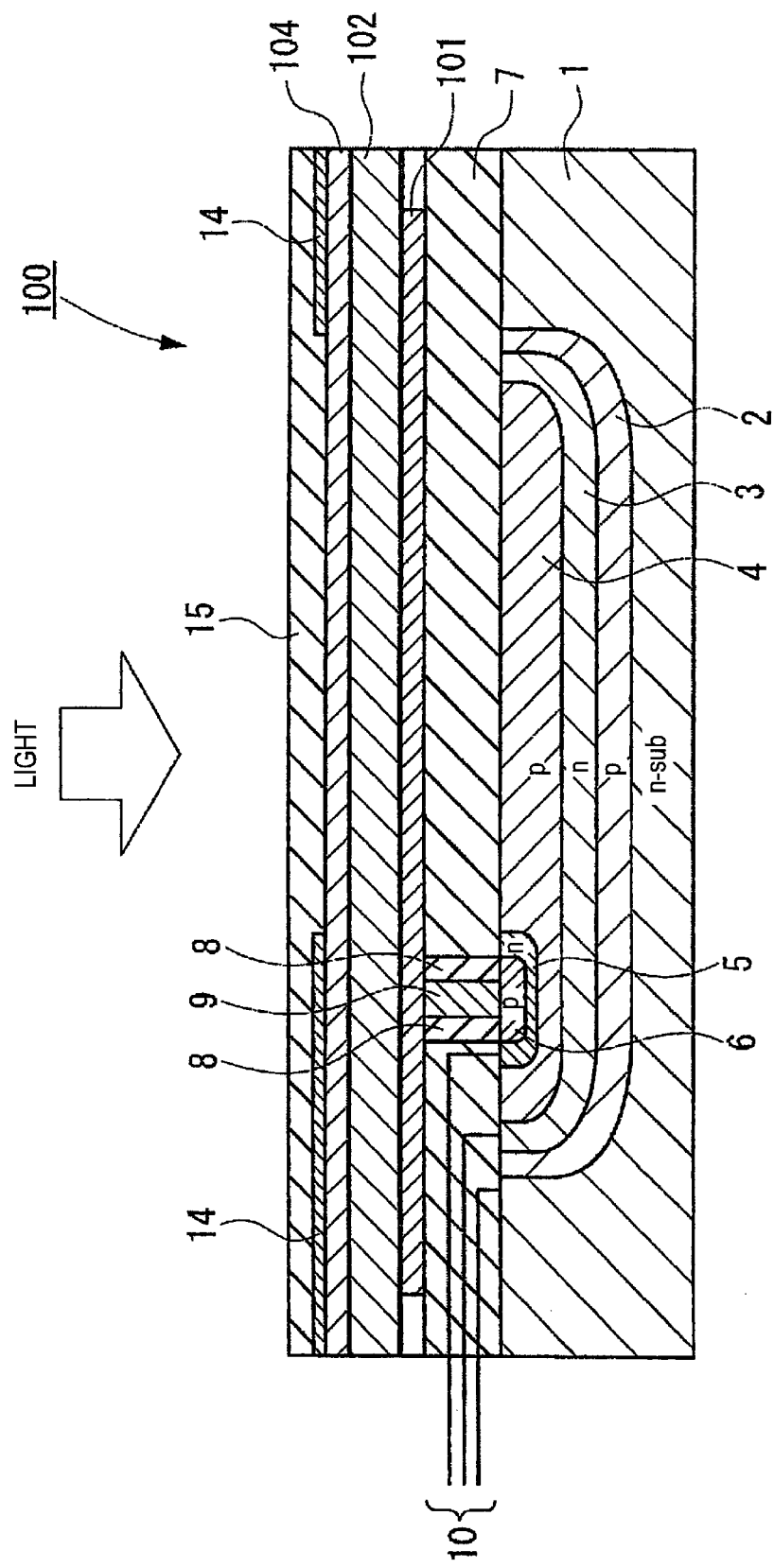
FIG. 2 is a schematic cross-sectional view of one pixel portion of an imaging device.

FIG. 2 is a schematic cross-sectional view of one pixel portion of an imaging device.

In the imaging device 100, a large number of pixels each constituting one pixel are disposed in an array manner in the same plane, and one-pixel data of the image data can be produced by the signals obtained from the one pixel.

One pixel of the imaging device shown in FIG. 2 is composed of an n-type silicon substrate 1, a transparent insulating film 7 formed on the n-type silicon substrate 1, and a photoelectric conversion device consisting of a lower electrode 101 formed on the insulating film 7, a photoelectric conversion layer 102 formed on the lower electrode 101 and a transparent electrode material-containing upper electrode 104 formed on the photoelectric conversion layer 102. A light-shielding film 14 having provided therein an opening is formed on the photoelectric conversion device, and a transparent insulating film 15 is formed on the upper electrode 104.

Inside the n-type silicon substrate 1, a p-type impurity region (hereinafter simply referred to as "p region") 4, an n-type impurity region (hereinafter simply referred to as "n region") 3, and a p region 2 are formed in order of increasing the depth. In the p region 4, a high-concentration p region 6 is formed in the surface part of the portion light-shielded by the light-shielding film 14, and the p region 6 is surrounded by an n region 5.

The depth of the pn junction plane between the p region 4 and the n region 3 from the surface of the n-type silicon substrate 1 is set to a depth at which blue light is absorbed (about 0.2 μm). Therefore, the p region 4 and the n region 3 form a photodiode (B photodiode) of absorbing blue light and accordingly accumulating electric charges.

The depth of the pn junction plane between the p region 2 and the n-type silicon substrate 1 from the surface of the n-type silicon substrate 1 is set to a depth at which red light is absorbed (about 2 μm). Therefore, the p region 2 and the n-type silicon substrate 1 form a photodiode (R photodiode) of absorbing red light and accordingly accumulating electric charges.

The p region 6 is electrically connected to the lower electrode 101 via a connection part 9 formed in the opening bored through the insulating film 7. A hole trapped by the lower electrode 101 recombines with an electron in the p region 6 and therefore, the number of electrons accumulated in the p region 6 on resetting decreases according to the number of holes trapped. The connection part 9 is electrically insulated by an insulating film 8 from portions except for the lower electrode 101 and the p region 6.

The electrons accumulated in the p region 2 are converted into signals according to the electric charge amount by an MOS circuit (not shown) composed of a p-channel MOS transistor formed inside the n-type silicon substrate 1, the electrons accumulated in the p region 4 are converted into signals according to the electric charge amount by an MOS circuit (not shown) composed of a p-channel MOS transistor formed inside the n region 3, the electrons accumulated in the p region 6 are converted into signals according to the electric charge amount by an MOS circuit (not shown) composed of a p-channel MOS transistor formed inside the n region 5, and these signals are output to the outside of the imaging device 100. Each MOS circuit is connected to a signal read-out pad (not shown) by a wiring 10. Incidentally, when an extractor electrode is provided in the p region 2 and p region 4 and a predetermined reset potential is applied, each region is depleted and the capacitance of each pn junction part becomes an infinitely small value, whereby the capacitance produced in the junction plane can be made extremely small.

Thanks to such a configuration, G light can be photoelectrically converted by the photoelectric conversion layer 102, and B light and R light can be photoelectrically converted by the B photodiode and the R photodiode, respectively, in the n-type silicon substrate 1. Also, since G light is first absorbed in the upper part, excellent color separation is achieved between B-G and between G-R. This is a greatly excellent point in comparison with an imaging device of the type where three PD are stacked inside a silicon substrate and all of BGR lights are separated inside the silicon substrate.

(Second Configuration Example of Imaging Device)

In this embodiment, instead of a configuration where two photodiodes are stacked inside a silicon substrate 1 as in the imaging device of FIG. 2, two photodiodes are arrayed in the direction perpendicular to the incident direction of incident light so that lights of two colors can be detected in the inside of the p-type silicon substrate.

Figure 3:
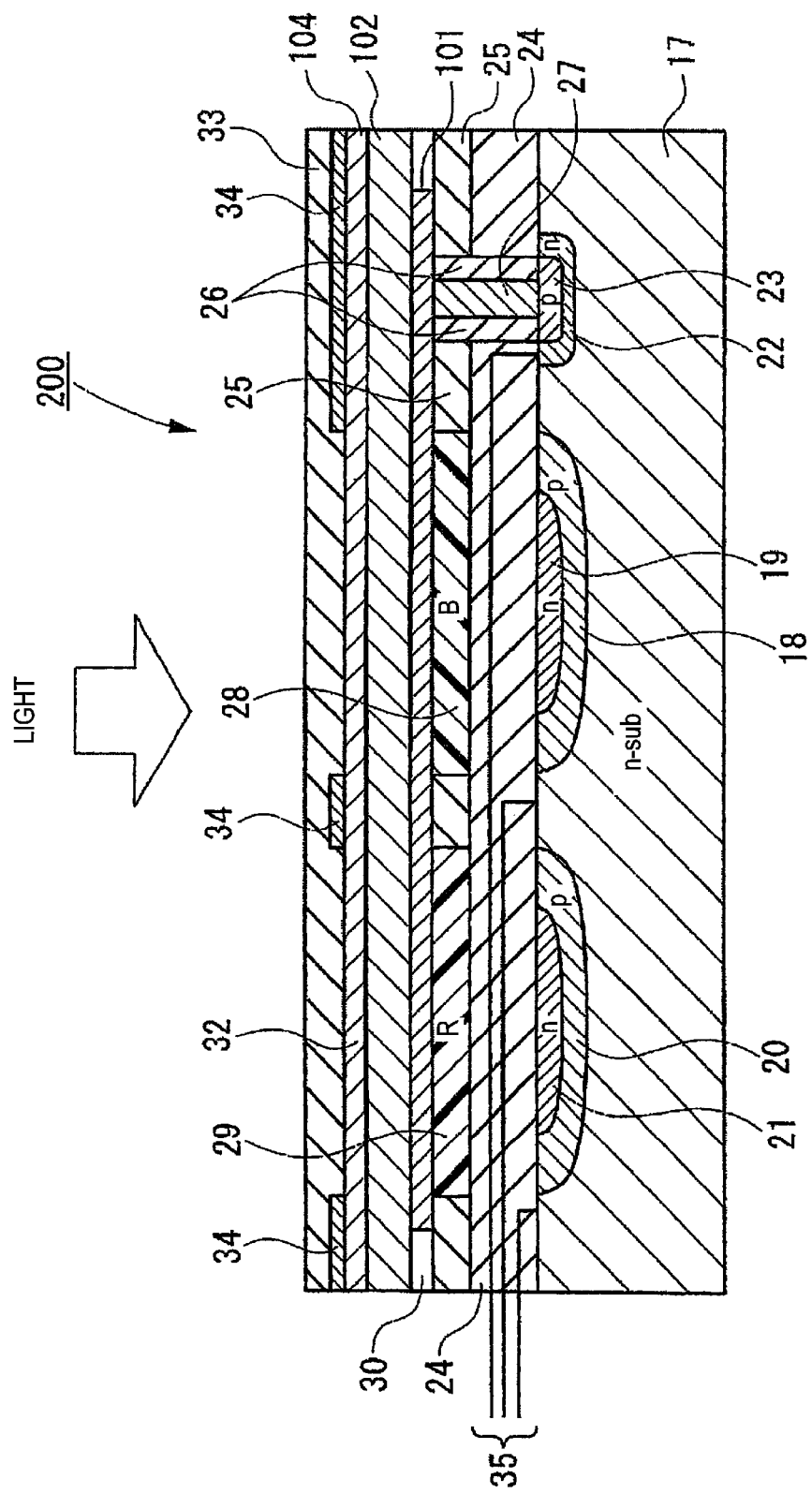
FIG. 3 is a schematic cross-sectional view of one pixel portion of an imaging device in another configuration example.

FIG. 3 is a schematic cross-sectional view of one pixel portion of an imaging device of this configuration example.

One pixel of the imaging device 200 shown in FIG. 3 is composed of an n-type silicon substrate 17 and a photoelectric conversion device consisting of a lower electrode 101 formed above the n-type silicon substrate 17, a photoelectric conversion layer 102 formed on the lower electrode 101, and an upper electrode 104 formed on the photoelectric conversion layer 102. A light-shielding film 34 having provided therein an opening is formed on the photoelectric conversion device, and a transparent insulating film 33 is formed on the upper electrode 104.

On the surface of the n-type silicon substrate 17 below the opening of the light-shielding film 34, a photodiode consisting of an n region 19 and a p region 18 and a photodiode consisting of an n region 21 and a p region 20 are formed to lie in juxtaposition on the surface of the n-type silicon substrate 17. An arbitrary plane direction on the n-type silicon substrate 17 surface becomes the direction perpendicular to the incident direction of incident light.

Above the photodiode consisting of an n region 19 and a p region 18, a color filter 28 capable of transmitting B light is formed via a transparent insulating film 24, and the lower electrode 101 is formed thereon. Above the photodiode consisting of an n region 21 and a p region 20, a color filter 29 capable of transmitting R light is formed via the transparent insulating film 24, and the lower electrode 101 is formed thereon. The peripheries of color filters 28 and 29 are covered with a transparent insulating film 25.

The photodiode consisting of an n region 19 and a p region 18 functions as an in-substrate photoelectric conversion part that absorbs B light transmitted through the color filter 28, accordingly generates electrons and accumulates the generated electrons in the p region 18. The photodiode consisting of an n region 21 and a p region 20 functions as an in-substrate photoelectric conversion part that absorbs R light transmitted through the color filter 29, accordingly generates electrons and accumulates the generated holes in the p region 20.

In the portion light-shielded by the light-shielding film 34 on the n-type silicon substrate 17 surface, a p region 23 is formed, and the periphery of the p region 23 is surrounded by an n region 22.

The p region 23 is electrically connected to the lower electrode 101 via a connection part 27 formed in the opening bored through the insulating films 24 and 25. A hole trapped by the lower electrode 101 recombines with an electron in the p region 23 and therefore, the number of electrons accumulated in the p region 23 on resetting decreases according to the number of holes trapped. The connection part 27 is electrically insulated by an insulating film 26 from portions except for the lower electrode 101 and the p region 23.

The electrons accumulated in the p region 18 are converted into signals according to the electric charge amount by an MOS circuit (not shown) composed of a p-channel MOS transistor formed inside the n-type silicon substrate 17, the electrons accumulated in the p region 20 are converted into signals according to the electric charge amount by an MOS circuit (not shown) composed of a p-channel MOS transistor formed inside the n-type silicon substrate 17, the electrons accumulated in the p region 23 are converted into signals according to the electric charge amount by an MOS circuit (not shown) composed of an n-channel MOS transistor formed inside the n region 22, and these signals are output to the outside of the imaging device 200. Each MOS circuit is connected to a signal read-out pad (not shown) by a wiring 35.

In this connection, instead of MOS circuits, the signal read-out part may be composed of CCD and an amplifier, that is, may be a signal read-out part where electrons accumulated in the p region 18, p region 20 and p region 23 are read out into CCD formed inside the n-type silicon substrate 17 and then transferred to an amplifier by the CCD and signals according to the electrons transferred are output from the amplifier.

In this way, the signal read-out part includes a CCD structure and a CMOS structure, but in view of power consumption, high-speed read-out, pixel addition, partial read-out and the like, CMOS is preferred.

Incidentally, in the imaging device of FIG. 3, color separation of R light and B light is performed by color filters 28 and 29, but instead of providing color filters 28 and 29, the depth of the pn junction plane between the p region 20 and the n region 21 and the depth of the pn junction plane between the p region 18 and the n region 19 each may be adjusted to absorb R light and B light by respective photodiodes.

An inorganic photoelectric conversion part composed of an inorganic material that absorbs light transmitted through the photoelectric conversion layer 102, accordingly generates electric charges and accumulates the electric charges, may also be formed between the n-type silicon substrate 17 and the lower electrode 101 (for example, between the insulating film 24 and the n-type silicon substrate 17). In this case, an MOS circuit for reading out signals according to the electric charges accumulated in a charge accumulation region of the inorganic photoelectric conversion part may be provided inside the n-type silicon substrate 17, and a wiring 35 may be connected also to this MOS circuit.

Also, there may take a configuration where one photodiode is provided inside the n-type silicone substrate 17 and a plurality of photoelectric conversion parts are stacked above the n-type silicon substrate 17; a configuration where a plurality of photodiodes are provided inside the n-type silicon substrate 17 and a plurality of photoelectric conversion parts are stacked above the n-type silicon substrate 17; or when a color image need not be formed, a configuration where one photodiode is provided inside the n-type silicon substrate 17 and only one photoelectric conversion part is stacked.

(Third Configuration Example of Imaging Device)

The imaging device of this embodiment has a configuration where a photodiode is not provided inside the silicon substrate and a plurality of (here, three) photoelectric conversion devices are stacked above the silicon substrate.

Figure 4:
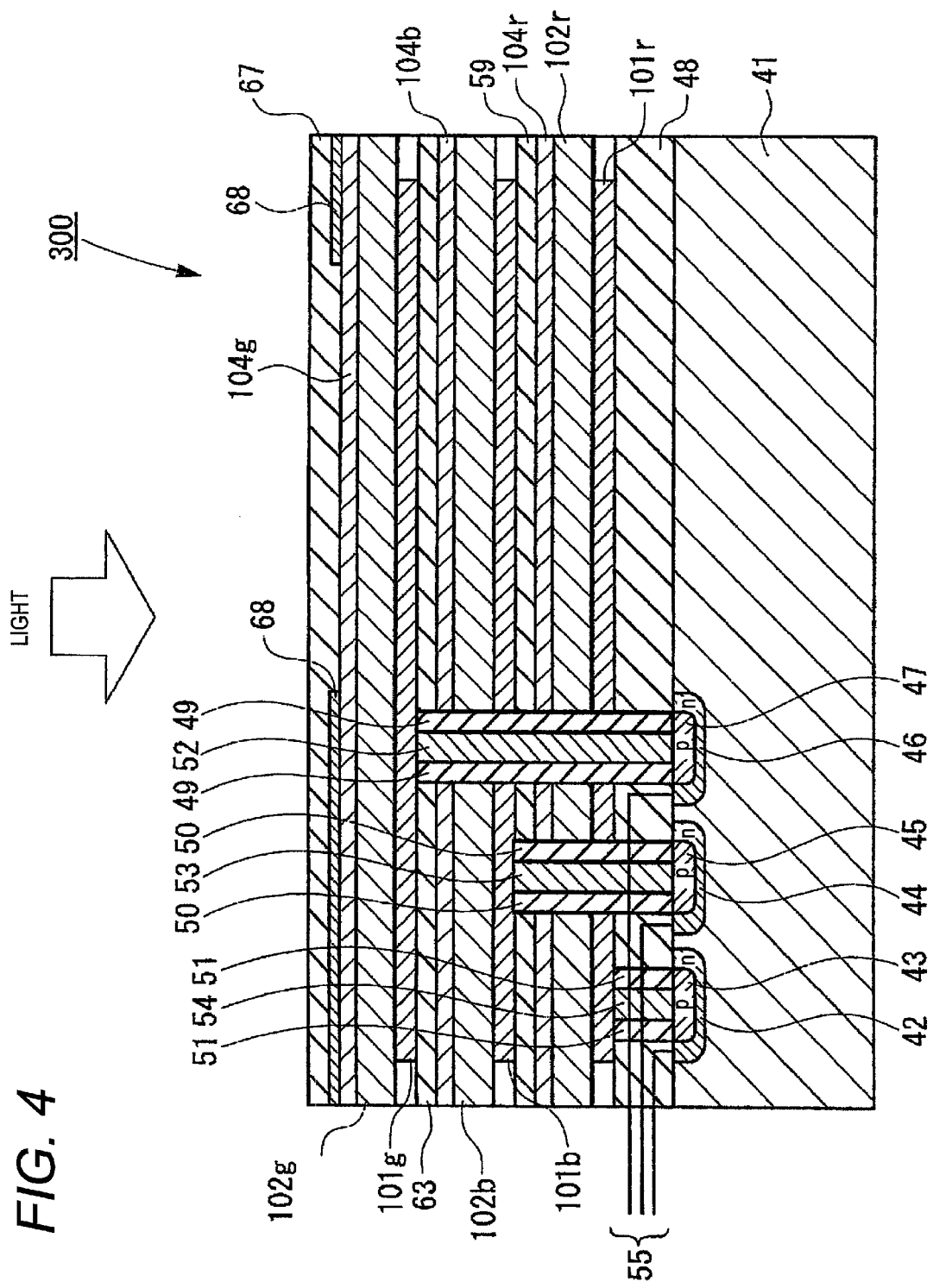
FIG. 4 is a schematic cross-sectional view of one pixel portion of an imaging device in another configuration example.

FIG. 4 is a schematic cross-sectional view of one pixel portion of the imaging device of this configuration example.

The imaging device 300 shown in FIG. 4 has a configuration where an R photoelectric conversion device, a B photoelectric conversion device, and a G photoelectric conversion device are stacked in order above a silicon substrate 41.

The R photoelectric conversion device is composed of, above the silicon substrate 41, a lower electrode 101r, a photoelectric conversion layer 102r formed on the lower electrode 101r, and an upper electrode 104r formed on the photoelectric conversion layer 102r.

The B photoelectric conversion device is composed of a lower electrode 101b stacked on the upper electrode 104r of the R photoelectric conversion device, a photoelectric conversion layer 102b formed on the lower electrode 101b, and an upper electrode 104b formed on the photoelectric conversion layer 102b.

The G photoelectric conversion device is composed of a lower electrode 101g stacked on the upper electrode 104b of the B photoelectric conversion device, a photoelectric conversion layer 102g formed on the lower electrode 101g, and an upper electrode 104g formed on the photoelectric conversion layer 102g. The imaging device of this configuration example has a configuration where the R photoelectric conversion device, the B photoelectric conversion device and the G photoelectric conversion device are stacked in this order.

A transparent insulating film 59 is formed between the upper electrode 104r of the R photoelectric conversion device and the lower electrode 101b of the B photoelectric conversion device, and a transparent insulating film 63 is formed between the upper electrode 104b of the B photoelectric conversion device and the lower electrode 101g of the G photoelectric conversion device. A light-shielding film 68 is formed in the region excluding an opening on the upper electrode 104g of the G photoelectric conversion device, and a transparent insulating film 67 is formed to cover the upper electrode 104g and the light-shielding film 68.

The lower electrode, the photoelectric conversion layer and the upper electrode contained in each of the R, G and B photoelectric conversion devices can have the same configuration as that in the photoelectric conversion device described above. However, the photoelectric conversion layer 102g contains an organic material capable of absorbing green light and accordingly generating electrons and holes, the photoelectric conversion layer 102b contains an organic material capable of absorbing blue light and accordingly generating electrons and holes, and the photoelectric conversion layer 102r contains an organic material capable of absorbing red light and accordingly generating electrons and holes.

In the portion light-shielded by the light-shielding film 68 on the silicon substrate 41 surface, p regions 43, 45 and 47 are formed, and the peripheries of these regions are surrounded by n regions 42, 44 and 46, respectively.

The p region 43 is electrically connected to the lower electrode 101r via a connection part 54 formed in an opening bored through an insulating film 48. A hole trapped by the lower electrode 101r recombines with an electron in the p region 43 and therefore, the number of electrons accumulated in the p region 43 on resetting decreases according to the number of holes trapped. The connection part 54 is electrically insulated by an insulating film 51 from portions except for the lower electrode 101r and the p region 43.

The p region 45 is electrically connected to the lower electrode 101b via a connection part 53 formed in an opening bored through the insulating film 48, the R photoelectric conversion device and the insulating film 59. A hole trapped by the lower electrode 101b recombines with an electron in the p region 45 and therefore, the number of electrons accumulated in the p region 45 on resetting decreases according to the number of holes trapped. The connection part 53 is electrically insulated by an insulating film 50 from portions except for the lower electrode 101b and the p region 45.

The p region 47 is electrically connected to the lower electrode 101g via a connection part 52 formed in an opening bored through the insulating film 48, the R photoelectric conversion device, the insulating film 59, the B photoelectric conversion device and the insulating film 63. A hole trapped by the lower electrode 101g recombines with an electron in the p region 47 and therefore, the number of electrons accumulated in the p region 47 on resetting decreases according to the number of holes trapped. The connection part 52 is electrically insulated by an insulating film 49 from portions except for the lower electrode 101g and the p region 47.

The electrons accumulated in the p region 43 are converted into signals according to the electric charge amount by an MOS circuit (not shown) composed of a p-channel MOS transistor formed inside the n region 42, the electrons accumulated in the p region 45 are converted into signals according to the electric charge amount by an MOS circuit (not shown) composed of a p-channel MOS transistor formed inside the n region 44, the electrons accumulated in the p region 47 are converted into signals according to the electric charge amount by an MOS circuit (not shown) composed of a p-channel MOS transistor formed inside the n region 46, and these signals are output to the outside of the imaging device 300. Each MOS circuit is connected to a signal read-out pad (not shown) by a wiring 55. Incidentally, instead of MOS circuits, the signal read-out part may be composed of CCD and an amplifier, that is, may be a signal read-out part where electrons accumulated in the p regions 43, 45 and 47 are read out into CCD formed inside the silicon substrate 41 and then transferred to an amplifier by the CCD and signals according to the electrons transferred are output from the amplifier.

In the description above, the photoelectric conversion layer capable of absorbing B light means a layer which can absorb at least light at a wavelength of 400 to 500 nm and in which the absorption factor at a peak wavelength in the wavelength region above is preferably 50% or more. The photoelectric conversion layer capable of absorbing G light means a layer which can absorb at least light at a wavelength of 500 to 600 nm and in which the absorption factor at a peak wavelength in the wavelength region above is preferably 50% or more. The photoelectric conversion layer capable of absorbing R light means a layer which can absorb at least light at a wavelength of 600 to 700 nm and in which the absorption factor at a peak wavelength in the wavelength region above is preferably 50% or more.

(Fourth Configuration Example of Imaging Device)

Figure 5:
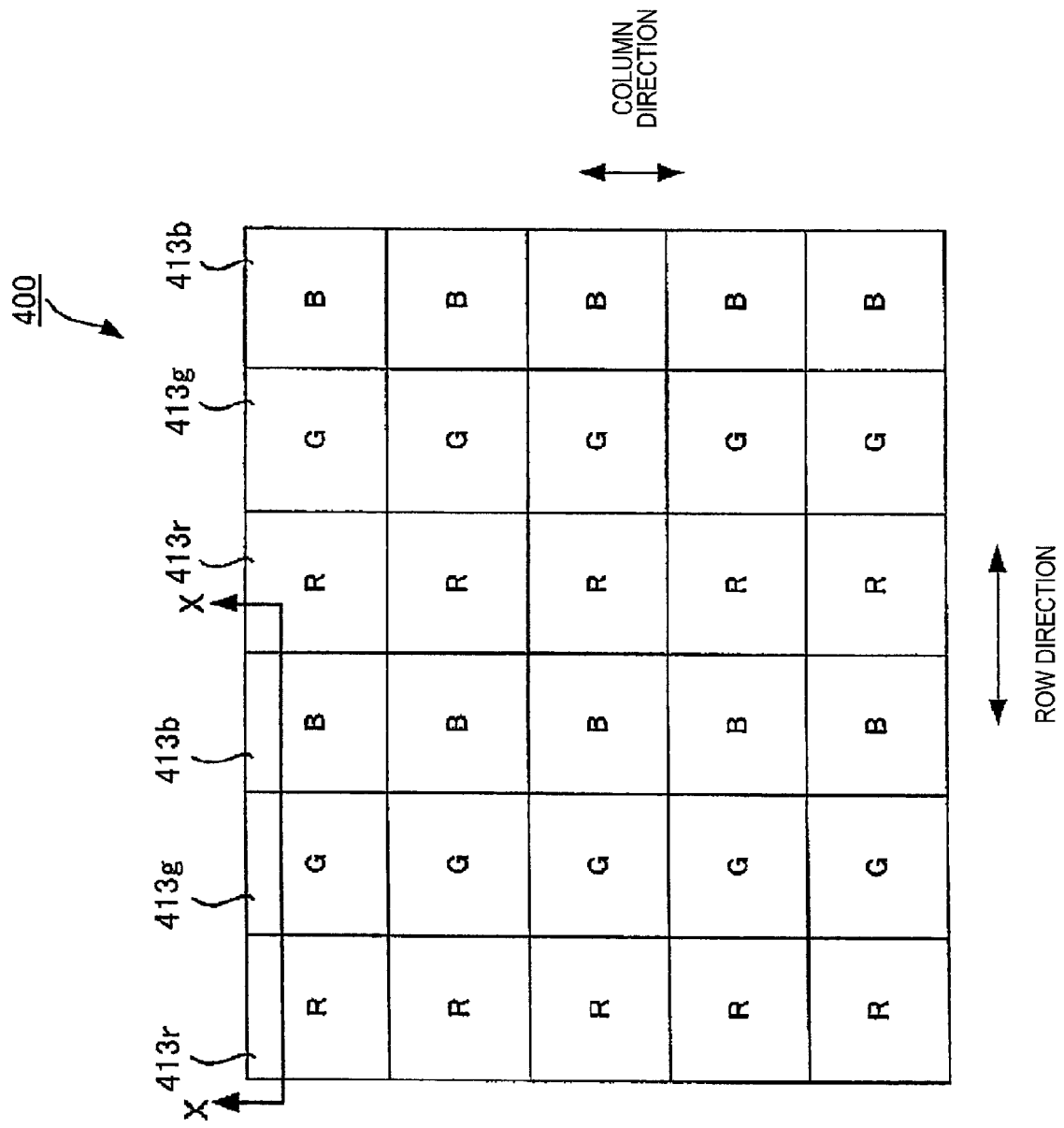
FIG. 5 is a schematic partial surface view of an imaging device in another configuration example.
Figure 6:
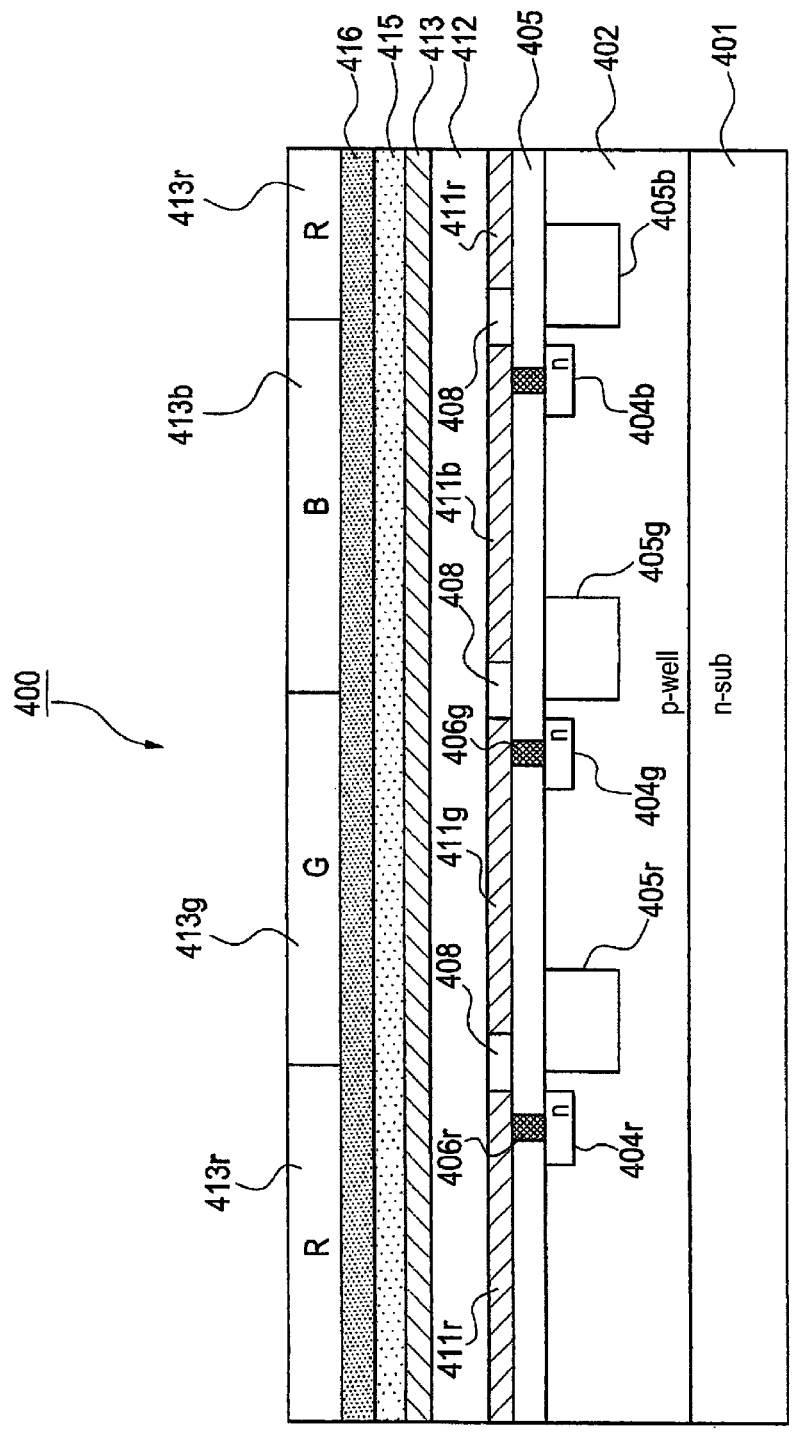
FIG. 6 is a schematic cross-sectional view cut along the X-X line of the imaging device shown in FIG. 5.

FIG. 5 is a schematic partial surface view of an imaging device for describing the embodiment of the present invention. FIG. 6 is a schematic cross-sectional view cut along the A-A line of the imaging device shown in FIG. 5.

A p-well layer 402 is formed on an n-type silicon substrate 401. In the following, the n-type silicon substrate 401 and the p-well layer 402 are collectively referred to as a semiconductor substrate. In the row direction and the column direction crossing with the row direction at right angles in the same plane above the semiconductor substrate, three kinds of color filters, that is, a color filter 413r mainly transmitting R light, a color filter 413g mainly transmitting G light, and a color filter 413b mainly transmitting B light, each is numerously arrayed.

As for the color filter 413r, a known material may be used, but the material transmits R light. As for the color filter 413g, a known material may be used, but the material transmits G light. As for the color filter 413b, a known material may be used, but the material transmits B light.

As for the array of color filters 413r, 413g and 413b, a color filter array used in known single-plate solid-state imaging devices (e.g., Bayer array, longitudinal stripe, lateral stripe) may be employed.

A transparent electrode 411r is formed above an n region 404r, a transparent electrode 411g is formed above an n region 404g, and a transparent electrode 411b is formed above an n region 404b. The transparent electrodes 411r, 411g and 411b are divided to correspond to the color filters 413r, 413g and 413b, respectively. The transparent electrodes 411r, 411g and 411b each has the same function as the lower electrode 11 of FIG. 1.

A photoelectric conversion film 412 in one-sheet configuration shared in common among the color filters 413r, 413g and 413b is formed on the transparent electrodes 411r, 411g and 411b.

An upper electrode 413 in one-sheet configuration shared in common among the color filters 413r, 413g and 413b is formed on the photoelectric conversion film 412.

A photoelectric conversion device corresponding to the color filter 413r is formed by the transparent electrode 411r, the upper electrode 413 opposing it, and a part of the photoelectric conversion film 412 sandwiched therebetween. This photoelectric conversion device is hereinafter referred to as an R photoelectric conversion device, because this device is formed on a semiconductor substrate.

A photoelectric conversion device corresponding to the color filter 413g is formed by the transparent electrode 411g, the upper electrode 413 opposing it, and a part of the photoelectric conversion film 412 sandwiched therebetween. This photoelectric conversion device is hereinafter referred to as a G photoelectric conversion device.

A photoelectric conversion device corresponding to the color filter 413b is formed by the transparent electrode 411b, the upper electrode 413 opposing it, and a part of the photoelectric conversion film 412 sandwiched therebetween. This photoelectric conversion device is hereinafter referred to as a B photoelectric conversion device.

In the n region inside the p-well layer 402, a high-concentration n-type impurity region (hereinafter referred to as an "n+ region") 404r for accumulating an electric charge generated in the photoelectric conversion film 412 of the on-substrate R photoelectric conversion device is formed. Incidentally, a light-shielding film is preferably provided on the n+ region 404r for preventing light from entering the n+ region 404r.

In the n region inside the p-well layer 402, an n+ region 404g for accumulating an electric charge generated in the photoelectric conversion film 412 of the on-substrate G photoelectric conversion device is formed. Incidentally, a light-shielding film is preferably provided on the n+ region 404g for preventing light from entering the n+ region 404g.

In the n region inside the p-well layer 402, an n+ region 404b for accumulating an electric charge generated in the photoelectric conversion film 412 of the on-substrate B photoelectric conversion device is formed. Incidentally, a light-shielding film is preferably provided on the n+ region 404b for preventing light from entering the n+ region 404b.

A contact part 406r composed of a metal such as aluminum is formed on the n+ region 404r, the transparent electrode 411r is formed on the contact part 406r, and the n+ region 404r and the transparent electrode 411r are electrically connected by the contact part 406r. The contact part 406r is embedded in an insulating layer 405 transparent to visible light and infrared light.

A contact part 406g composed of a metal such as aluminum is formed on the n+ region 404g, the transparent electrode 411g is formed on the contact part 406g, and the n+ region 404g and the transparent electrode 411g are electrically connected by the contact part 406g. The contact part 406g is embedded in the insulating layer 405.

A contact part 406b composed of a metal such as aluminum is formed on the n+ region 404b, the transparent electrode 411b is formed on the contact part 406b, and the n+ region 404b and the transparent electrode 411b are electrically connected by the contact part 406b. The contact part 406b is embedded in the insulating layer 405.

Inside the p-well layer 402, in the region other than those where the n+ regions 404r, 404g and 404b are formed, a signal read-out part 405r for reading out signals according to electric charges generated in the R photoelectric conversion device and accumulated in the n+ region 404r, a signal read-out part 405g for reading out signals according to electric charges generated in the G photoelectric conversion device and accumulated in the n+ region 404g, and a signal read-out part 405b for reading out signals according to electric charges generated in the B photoelectric conversion device and accumulated in the n+ region 404b are formed. For each of the signal read-out parts 405r, 405g and 405b, a known configuration using a CCD or MOS circuit may be employed.

A two-layer structure of protective layers 415 and 416 for protecting the on-substrate photoelectric conversion devices is formed on the photoelectric conversion film 412, and color filters 413r, 413g and 413b are formed on the protective layer 416.

When a predetermined bias voltage is applied to the transparent electrode 411r and the upper electrode 413, electric charges generated in the photoelectric conversion film 412 constituting the on-substrate R photoelectric conversion device move to the n+ region 404r through the transparent electrode 411r and the contact part 406r and are accumulated therein. Signals according to electric charges accumulated in the n+ region 404r are read out by the signal read-out part 405r and output to the outside of the imaging device 400.

Similarly, when a predetermined bias voltage is applied to the transparent electrode 411g and the upper electrode 413, electric charges generated in the photoelectric conversion film 412 constituting the on-substrate G photoelectric conversion device move to the n+ region 404g through the transparent electrode 411g and the contact part 406g and are accumulated therein. Signals according to electric charges accumulated in the n+ region 404g are read out by the signal read-out part 405g and output to the outside of the imaging device 400.

Also, similarly, when a predetermined bias voltage is applied to the transparent electrode 411b and the upper electrode 413, electric charges generated in the photoelectric conversion film 412 constituting the on-substrate B photoelectric conversion device move to the n+ region 404b through the transparent electrode 411b and the contact part 406b and are accumulated therein. Signals according to electric charges accumulated in the n+ region 404b are read out by the signal read-out part 405b and output to the outside of the imaging device 400.

In this way, the imaging device 400 can output, to the outside, signals of an R component according to electric charges generated in the R photoelectric conversion device, signals of a G component according to electric charges generated in the G photoelectric conversion device, and signals of a B component according to electric charges generated in the B photoelectric conversion device, whereby a color image can be obtained. Thanks to this mode, the photoelectric conversion part becomes thin, so that resolution can be enhanced and a false color can be reduced. Also, the aperture ratio can be made large irrespective of the lower circuit and therefore, high sensitivity can be achieved. Furthermore, a microlens can be omitted and this is effective in reducing the number of components.

In this embodiment, the organic photoelectric conversion film needs to have a maximum absorption wavelength in the green light region and have an absorption region over the entire visible light, but this can be preferably realized by the materials specified above of the present invention.

EXAMPLES

The present invention is described in greater detail below by referring to Examples, but the present invention is not limited to these Examples.

Example 1

<Synthesis of Compound (5)>

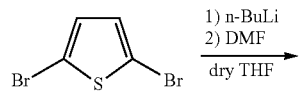

1) n-BuLi
2) DMF
dry THF

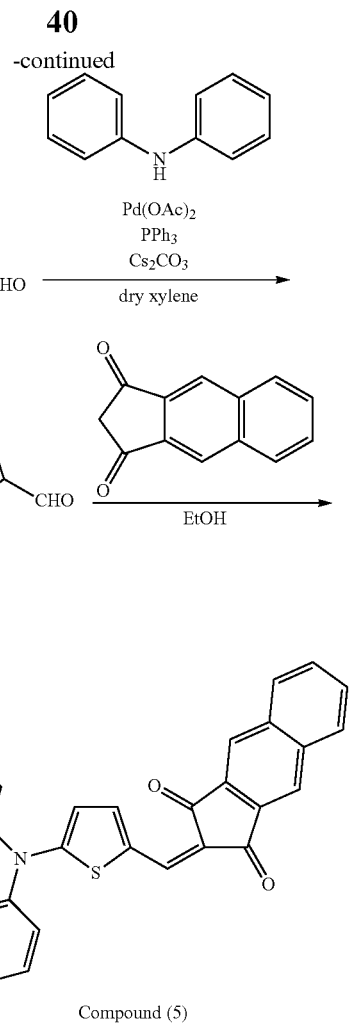

Compound (5)

(Synthesis of Compound 5a)

2,5-Dibromothiophene (produced by Tokyo Chemical Industry Co., Ltd.) (3.0 ml) was dissolved in 100 ml of dehydrated THF, and the solution was adjusted to an inner temperature of −78° C. in a dry ice bath. Subsequently, 19.2 ml of n-BuLi was slowly added dropwise and after 5 minutes, 5.1 ml of dehydrated DMF was gradually added dropwise. Thereafter, the dry ice bath was removed, and the inner temperature was raised to room temperature. After adding 2 N HCl, extraction with ethyl acetate was performed, and the oil layer was washed with 1 N HCl and aq. NaCl, then dried over sodium sulfate and filtered. The obtained reaction mixture was separated on a silica gel column (developing solution: AcOEt/n-Hexane=1/4), and the solvent was distilled off to obtain 1.3 g of Compound (5a).

(Synthesis of Compound 5b)

Compound (5a) (1.0 g), 1.8 g of diphenylamine (produced by Tokyo Chemical Industry Co., Ltd.), 3.4 g of cesium carbonate, 59 mg of palladium acetate and 0.34 g of triphenylphosphine were added to 17 ml of dehydrated xylene, and the mixture was refluxed for 5 hours. The resulting reaction mixture was suction-filtered and after distilling off the solvent, purified on a silica gel column (developing solvent: toluene). The solvent was removed by distillation to obtain 0.3 g of Compound (5b).

(Synthesis of Compound (5))

Compound (5b) (250 mg) and 210 mg of benzindandione were added to 5 ml of ethanol, and the mixture was refluxed for 3 hours. The resulting reaction mixture was allowed to cool and then suction-filtered, and the filter cake was dissolved in a small amount of chloroform, recrystallized from ethanol and then suction-filtered to obtain 199 mg of Compound (5). The compound was identified by ¹H-NMR.

<Identification of Compound (5)>

¹H-NMR (CDCl₃) δ: 6.49 (1H, d), 7.30-7.49 (10H, m), 7.58-7.64 (2H, m), 7.75 (1H, br), 7.89 H, s), 8.00 (2H, m), 8.25 (1H, s), 8.32 (1H, s).

Molecular weight: 457.54

<Measurement of Melting Point>

The melting point of Compound (5) was measured using TG/DTA 6200 AST-2 manufactured by SII NanoTechnology Inc. and found to be 311° C.

<Measurement of Absorption Spectrum and Molar Extinction Coefficient>

The absorption spectrum (in a chloroform solution) of Compound (5) was measured using UV-2550 manufactured by Shimadzu Corporation, as a result, the peak wavelength was 549 nm and the molar extinction coefficient at this wavelength was 88,000

<Fabrication of Photoelectric Conversion Device>

In the embodiment of FIG. 1A, amorphous ITO was deposited on a CMOS substrate by sputtering to a thickness of 30 nm and patterned by photolithography so as to allow one pixel to be present for each photodiode (PD) on the CMOS substrate, thereby forming a pixel electrode, EB-3 was then deposited by vacuum heating deposition to a thickness of 100 nm, a layer formed by co-depositing Compound (5) and fullerene ($C_{60}$) to a thickness of 100 nm and 300 nm, respectively, in terms of a single layer was deposited thereon by vacuum heating deposition to form a photoelectric conversion layer, and amorphous ITO as an upper electrode was further deposited by sputtering to a thickness of 5 nm to form a transparent electrode. In this way, a solid-state imaging device was fabricated. After forming an SiO film as a protective layer by heating vapor deposition on the upper electrode, an $Al_2O_3$ layer was formed thereon by an ALCVD method. For all layers of the photoelectric conversion layer 12, the vacuum deposition was performed at a vacuum degree of $4 \times 10^{-4}$ Pa or less.

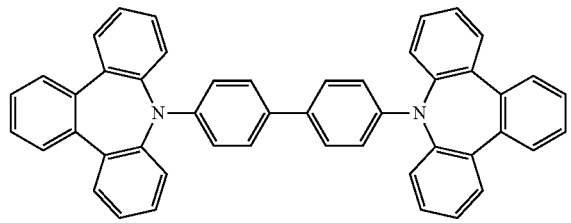

EB-3; Ea = 1.9 eV, Ip = 5.2 eV

Example 2

<Synthesis of Compound (8)>

Compound (8) was synthesized by the same synthesis method as that for Compound (5) except for changing diphenylamine to 1,2'-dinaphthylamine (produced by Tokyo Chemical Industry Co., Ltd.).

<Fabrication of Photoelectric Conversion Device>

A solid-state imaging device was fabricated in the same manner as in Example 1 except for changing Compound (5) in the photoelectric conversion layer 12 to Compound (8).

Example 3

<Synthesis of Compound (18)>

Compound (18) was synthesized by the same synthesis method as that for Compound (5) by using 2,5-dibromothieno[3,2-b]thiophene (produced by Tokyo Chemical Industry Co., Ltd.) as the starting material. The compound was identified by ¹H-NMR.

<Identification of Compound (18)>

¹H-NMR (CDCl₃) δ: 6.65 (1H, s), 7.26-7.43 (10H, m), 7.65 (2H, m), 8.00 (1H, s), 8.07 (2H, m), 8.23 (111, br), 8.39 (2H, d).

Molecular weight: 513.63

<Measurement of Absorption Spectrum and Molar Extinction Coefficient>

The peak wavelength of the absorption spectrum and the molar extinction coefficient thereof were determined by the same operation as in Example 1, as a result, the peak wavelength of the absorption spectrum was 536 nm and the molar extinction coefficient at this wavelength was 94,000 $M^{-1}$ $cm^{-1}$.

<Fabrication of Photoelectric Conversion Device>

A solid-state imaging device was fabricated in the same manner as in Example 1 except for changing Compound (5) in the photoelectric conversion layer 12 to Compound (18).

Example 4

<Synthesis of Compound (19)>

Compound (19) was synthesized by the same synthesis method as that for Compound (18) except for changing diphenylamine to N-phenyl-2-naphthylamine (produced by Tokyo Chemical Industry Co., Ltd.).

<Fabrication of Photoelectric Conversion Device>

A solid-state imaging device was fabricated in the same manner as in Example 1 except for changing Compound (5) in the photoelectric conversion layer 12 to Compound (19).

Example 5

<Synthesis of Compound (34)>

Compound (34) was synthesized by the same synthesis method as that for Compound (5) except for changing diphenylamine to N-phenyl-2-naphthylamine (produced by Tokyo Chemical Industry Co., Ltd.) and changing benzindandione to sodium thiobarbiturate (produced by Tokyo Chemical Industry Co., Ltd.).

<Fabrication of Photoelectric Conversion Device>

A solid-state imaging device was fabricated in the same manner as in Example 1 except for changing Compound (5) in the photoelectric conversion layer 12 to Compound (34).

Comparative Example 1

A solid-state imaging device was fabricated in the same manner as in Example 1 except for changing the photoelectric conversion layer 12 to a layer formed by depositing Comparative Compound (1) alone to a thickness of 100 nm.

Comparative Compound (1)

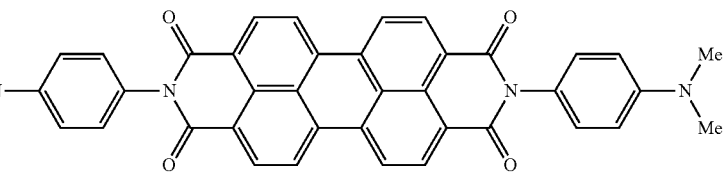

Comparative Example 2

Fabrication of a solid-state imaging device was attempted in the same manner as in Comparative Example 1 except for changing Comparative Compound (1) to Comparative Compound (2), but the vapor deposition rate was not stabilized during deposition of the photoelectric conversion layer, failing in forming the layer with the above-described thickness, and a solid-state imaging device could not be fabricated.

Comparative Compound (2):

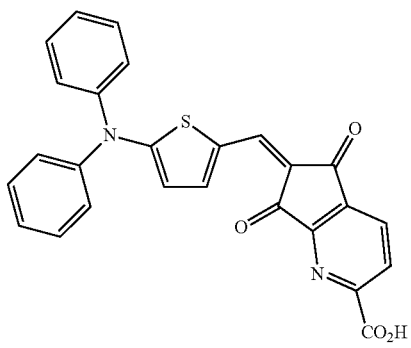 [SMILES: O=C(O)c1ccc2c(n1)C(=O)/C(=C\c1ccc(N(c3ccccc3)c3ccccc3)s1)C2=O]

Comparative Example 3

A solid-state imaging device was fabricated in the same manner as in Comparative Example 1 except for changing Comparative Compound (1) to Comparative Compound (3), as a result, the photoelectric conversion efficiency and the dark current could not be measured due to crystallization of the photoelectric conversion film.

Comparative Compound (3):

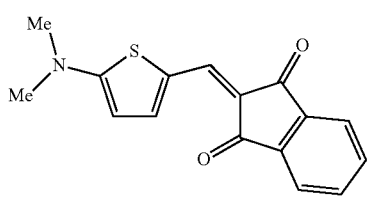 [SMILES: CN(C)c1ccc(C=C2C(=O)c3ccccc3C2=O)s1]

The external quantum efficiency at the maximum sensitivity wavelength when the dark current in each of the devices of Examples 1 to 5 and Comparative Example 1 was 400 pA/cm$^2$ is shown in Table 1. Incidentally, at the time of measuring the photoelectric conversion performance of each device, an appropriate voltage was applied.

The molar extinction coefficient of the compound used in each of the devices of Examples 1 to 5 and Comparative Example 1 was determined. The results are shown in Table 1.

TABLE 1

| Compound Used for Light-Absorbing/Photoelectric Conversion Material | External Quantum Efficiency at Maximum Sensitivity Wavelength with Dark Current of 400 pA/cm$^2$ (relative value) | Molar Extinction Coefficient (relative value) |
|---|---|---|
| Example 1 | Compound (5) and C$_{60}$ | 100 | 94 |
| Example 2 | Compound (8) and C$_{60}$ | 100 | 95 |
| Example 3 | Compound (18) and C$_{60}$ | 100 | 98 |
| Example 4 | Compound (19) and C$_{60}$ | 100 | 100 |
| Example 5 | Compound (34) and C$_{60}$ | 98 | 70 |
| Comparative Example 1 | Comparative Compound (1) | <1 | 47 |

As seen from Table 1, according to the present invention, a solid-state imaging device having high photoelectric coefficient can be obtained.

The entire disclosure of Japanese Patent Application No. 2009-225522 filed on Sep. 29, 2009, from which the benefit of foreign priority has been claimed in the present application, is incorporated herein by reference, as if fully set forth.

What is claimed is:

1. A compound represented by the following formula (4):

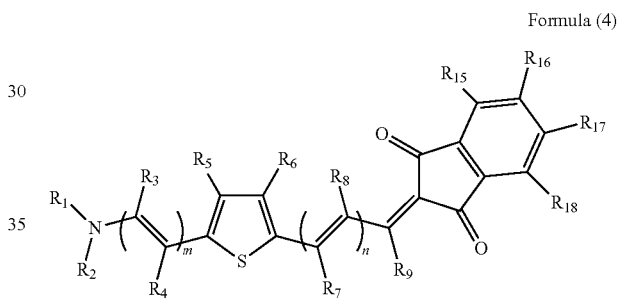

Formula (4)

wherein each of $R_1$ and $R_2$ independently represents a substituted aryl group, an unsubstituted aryl group, a substituted heteroaryl group or an unsubstituted heteroaryl group, each of $R_3$ to $R_9$ and $R_{15}$ to $R_{18}$ independently represents a hydrogen atom or a substituent, m represents 0 or 1, and n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, $R_{15}$ and $R_{16}$, $R_{16}$ and $R_{17}$, or $R_{17}$ and $R_{18}$ may be combined with each other to form a ring, provided that if $R_7$ and $R_9$ combine with each other to form a ring, then the ring is selected from the group consisting of a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring and a phenazine ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

2. A photoelectric conversion device comprising an electrically conductive film, an organic photoelectric conversion film, and a transparent electrically conductive film, wherein the organic photoelectric conversion film contains the compound according to claim 1.

3. A photosensor comprising the photoelectric conversion device according to claim 2.

4. An imaging device containing the photoelectric conversion device according to claim 2.

5. A compound represented by the following formula (5):

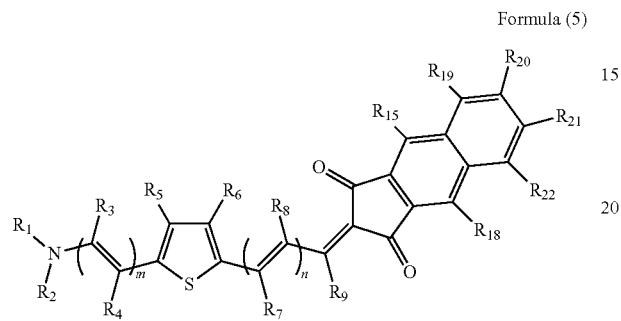

Formula (5)

wherein each of $R_1$ and $R_2$ independently represents a substituted aryl group, an unsubstituted aryl group, a substituted heteroaryl group or an unsubstituted heteroaryl group, each of $R_3$ to $R_9$, $R_{15}$ and $R_{18}$ to $R_{22}$ independently represents a hydrogen atom or a substituent, m represents 0 or 1, and n represents an integer of 0 or more, $R_1$ and $R_2$, $R_3$ and $R_4$, $R_3$ and $R_5$, $R_5$ and $R_6$, $R_6$ and $R_8$, $R_7$ and $R_8$, $R_7$ and $R_9$, $R_{15}$ and $R_{19}$, $R_{19}$ and $R_{20}$, $R_{20}$ and $R_{21}$, $R_{21}$ and $R_{22}$, or $R_{22}$ and $R_{18}$ may be combined with each other to form a ring, provided that if $R_7$ and $R_9$ combine with each other to form a ring, then the ring is selected from the group consisting of a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring and a phenazine ring, and when n is an integer of 2 or more, out of a plurality of $R_7$'s and $R_8$'s, a pair of $R_7$'s, a pair of $R_8$'s, or a pair of $R_7$ and $R_8$ may be combined each other to form a ring.

* * * * *